US008895579B2

(12) United States Patent
Swanson et al.

(10) Patent No.: US 8,895,579 B2
(45) Date of Patent: Nov. 25, 2014

(54) HETEROTRICYCLIC AMPA RECEPTOR ANTAGONISTS FOR TREATMENT OF EPILEPSY, PAIN, AND OTHER NEUROLOGICAL DISORDERS AND DISEASES

(75) Inventors: Geoffrey T. Swanson, Oak Park, IL (US); Martin B. Gill, Indianapolis, IN (US); Ryuichi Sakai, Hakodate (JP); Masato Oikawa, Kanagawa (JP)

(73) Assignee: Northwestern University, Evanston, IL (US)

( * ) Notice: Subject to any disclaimer, the term of this patent is extended or adjusted under 35 U.S.C. 154(b) by 415 days.

(21) Appl. No.: 13/052,742

(22) Filed: Mar. 21, 2011

(65) Prior Publication Data

US 2012/0071423 A1 Mar. 22, 2012

Related U.S. Application Data

(60) Provisional application No. 61/315,636, filed on Mar. 19, 2010.

(51) Int. Cl.
*A61K 31/437* (2006.01)
*A61K 31/407* (2006.01)
*A61K 31/4355* (2006.01)

(52) U.S. Cl.
CPC ............. *A61K 31/437* (2013.01); *A61K 31/407* (2013.01)
USPC .............................. 514/293; 514/290; 546/81

(58) Field of Classification Search
CPC A61K 31/407; A61K 31/437; A61K 31/4355
USPC ............. 546/81; 514/290, 293; 548/430, 431, 548/432
See application file for complete search history.

(56) References Cited

U.S. PATENT DOCUMENTS

2009/0118358 A1 5/2009 Swanson et al.

OTHER PUBLICATIONS

Alexander et al., Guide to Receptors and Channels (GRAC), 3rd edition, British Journal of Pharmacology, 2008, 153(Suppl. 2):S1-S209.
Ben-Ari, "Cell death and synaptic reorganization produced by seizures", Epilepsia, 2001, 42(Suppl. 3): 5-7.
Contractor et al., "Loss of Kainate Receptor-Mediated Heterosynaptic Facilitation of Mossy-Fiber Synapses in KA2 Mice", The Journal of Neuroscience, Jan. 15, 2003, 23(2):422-429.
Cordier et al., "Natural products as an inspiration in the diversity-oriented synthesis of bioactive compound libraries", Nat Prod Rep, Aug. 2008, 25(4):719-737.
Deshpande et al., "In vitro status epilepticus but not spontaneous recurrent seizures cause cell death in cultured hippocampal neurons", Epilepsy Res, Jul. 2007, 75(2-3):171-179.
Fernandes et al., "High affinity kainate receptor subunits are necessary for ionotropic but not metabotropic signaling", Neuron, Sep. 24, 2009, 63(6):818-829.
Gigler et al., "Neuroprotective and anticonvulsant effects of EGIS-8332, a non-competitive AMPA receptor antagonist, in a range of animal models", British Journal of Pharmacology, 2007, 152:151-160.
Gill et al., "A series of structurally novel heterotricyclic AMPA receptor-selective antagonist", Br. J. Pharmacol., Jul. 2010, 160(6):1417-29.
Greene et al., "Protection from fatal viral encephalomyelitis: AMPA receptor antagonists have a direct effect on the inflammatory response to infection", PNAS, Mar. 4, 2008, 105(9):3575-3580.
Grossman et al., "Talampanel with standard radiation and temozolomide in patients with newly diagnosed glioblastoma: a multicenter phase II trial", Journal of Clinical Oncology, Sep. 1, 2009, 27(25):4155-4161.
Hirbec et al., "Rapid and differential regulation of AMPA and Kainate Receptors at Hippocampal Mossy Fibre Synapses by PICK1 and GRIP", Neuron, Feb. 20, 2003, 37:625-638.
Hollman et al., "Cloned Glutamate Receptors", Annu. Rev. Neurosci., 1994, 17:31-108.
Ikoma et al., "Regioselective Domino Metathesis of 7-Oxanorbornenes and Its Application to the Synthesis of Biologically Active Glutamate Analogues", Eur. J. Org. Chem., 2008, 5215-5220.
Ito et al., "Attenuated Plasticity of Postsynaptic Kainate Receptors in Hippocampal CA3 Pyramidal Neurons", The Journal of Neuroscience, Jul. 7, 2004, 24(27):6228-6236.
Keller et al., "Identification of a subunit-specific antagonist of alpha-amino-3-hydroxy-5-methyl-4-isoxazolepropionate/kainate receptor channels", PNAS, Jan. 1993, 90:605-609.
Lash et al., "Novel Analogs and Stereoisomers of the Marine Toxin Neodysiherbaine with Specificity for Kainate Receptors", J Pharmacol Exp Ther, Feb. 2008, 324(2):484-496.
Lu et al., "Subunit Composition of Synaptic AMPA Receptors Revealed by a Single-Cell Genetic Approach", Neuron, Apr. 30, 2009, 62:254-268.
Malinow et al., "AMPA Receptor Trafficking and Synaptic Plasticity", Annu. Rev. Neurosci., 2002, 25:103-126.
Mony et al., "Allosteric modulators of NR2B-containing NMDA receptors: molecular mechanisms and therapeutic potential", British Journal of Pharmacology, 2009, 157:1301-1317.
Mulle et al., "Altered synaptic physiology and reduced susceptibility to kainate-induced seizures in GluR6-deficient mice", Nature, Apr. 9, 1998, 392:601-605.

(Continued)

*Primary Examiner* — Rita Desai
(74) *Attorney, Agent, or Firm* — Andrus Intellectual Property Law, LLP

(57) ABSTRACT

Disclosed are heterotricyclic compounds, pharmaceutical compositions, methods of treatment, and methods for selectively antagonizing a glutamate receptor. The pharmaceutical compositions may include and the methods may utilize heterotricyclic compounds that are glutamate analogues which have specificity for AMPA receptors. The pharmaceutical compositions may be utilized to treat or prevent neurological diseases or disorders.

4 Claims, 9 Drawing Sheets

(56) References Cited

OTHER PUBLICATIONS

Nelson et al., "Strength through diversity", Neuron, Nov. 6, 2008, 60:477-482.

Oikawa et al., "Regioselective Domino Metathesis of Unsymmetrical 7-Oxanorbornenes with Electron-Rich Vinyl Acetate toward Biologically Active Glutamate Analogues", European J Org Chem, Nov. 1, 2009, 2009 (32):5531-5548.

Patneau et al., "Hippocampal Neurons Exhibit Cyclothiazide-sensitive Rapidly Desensitizing Responses to Kainate", The Journal of Neuroscience, Aug. 1993, 13(8):3496-3509.

Sakai et al., "Dysiherbaine: A New Neurotoxic Amino Acid from the Micronesian Marine Sponge Dysidea herbacea", J. Am. Chem. Soc., 1997, 119:4112-4116.

Sakai et al., "Pharmacological Properties of the Potent Epileptogenic Amino Acid Dysiherbaine, a Novel Glutamate Receptor Agonist Isolated from the Marine Sponge Dysidea herbacea", The Journal of Pharmacology and Experimental Therapeutics, 2001, 296(2):650-658.

Sanders et al., "Divergent Pharmacological Activity of Novel Marine-Derived Excitatory Amino Acids on Glutamate Receptors", The Journal of Pharmacology and Experimental Therapeutics, 2005, 314(3):1068-1078.

Smith et al., "Autoimmune encephalomyelitis ameliorated by AMPA antagonists", Nature Medicine, Jan. 2000, 6(1):62-66.

Stern-Bach et al., "A Point Mutation in the Glutamate Binding Site Blocks Desensitization of AMPA Receptors", Neuron, Oct. 1998, 21:907-918.

Swanson et al., "Ligands for Ionotropic Glutamate Receptors", Prog Mol Subcell Biol, 2009, 46:123-157.

Tan, "Diversity-oriented synthesis: exploring the intersections between chemistry and biology", Nature Chemical Biology, Jul. 2005, 1(2):74-84.

Vivithanaporn et al., "Critical Roles for the M3-S2 Transduction Linker Domain in Kainate Receptor Assembly and POstassembly Trafficking", The Journal of Neuroscience, Sep. 26, 2007, 27(39):10423-10433.

Wilding et al., "Differential Antagonism of alpha-amino-3-hydroxy-5-methyl-4-isoxazolepropionic acid-preferring and kainate-preferring receptors by 2,3-benzodiazepines", Molecular Pharmacology, 1995, 47:582-587.

HETEROTRICYCLIC AMPA RECEPTOR ANTAGONISTS FOR TREATMENT OF EPILEPSY, PAIN, AND OTHER NEUROLOGICAL DISORDERS AND DISEASES

CROSS-REFERENCE TO RELATED APPLICATIONS

This application claims the benefit under 35 U.S.C. §119(e) to U.S. Provisional Application No. 61/315,636, filed on Mar. 19, 2010, the contents of which are incorporated herein by reference in their entirety.

STATEMENT REGARDING FEDERALLY SPONSORED RESEARCH OR DEVELOPMENT

This invention was made with government support under grant number R01NS044322 awarded by the National Institutes of Health. The government has certain rights in the invention.

BACKGROUND

Glutamate receptors are the primary mediators of excitatory synaptic transmission in the central nervous system. Glutamate is one of the twenty (20) common amino acids, but it is also functions as a ligand for glutamate receptors. Glutamate is particularly abundant in the nervous system where it functions as a neurotransmitter. Glutamate receptors are responsible for the glutamate-mediated post-synaptic excitation of neural cells, and are important for neural functions including neural communication, memory formation, learning, and physiological regulation. Accordingly, glutamate receptors have been implicated in the pathologies of a number of neurological diseases and disorders.

Glutamate receptors can be divided into two groups based on the mechanism by which their activation gives rise to a post-synaptic current. "Ionotropic" glutamate receptors (iGluRs) form an ion channel pore that is activated when glutamate binds to the receptor. "Metabotropic" glutamate receptors (mGluRs) indirectly activate ion-channels on the plasma membrane through a signaling cascade that involves G-proteins.

There are many specific subtypes of glutamate receptors, and it is customary in the field to refer to receptor subtypes by a chemical agonist which binds to the receptor more selectively than glutamate. Agonists include kainate which is a salt of kainic acid, N-methyl-D-Aspartate (NMDA), and α-amino-3-hydroxyl-5-methyl-4-isoxazole-propionate (AMPA).

Kainate receptors (KARs), one subgroup of the ionotropic glutamate receptor family, have roles in brain physiology and pathology that are poorly characterized. Natural source compounds have been useful tools for identification and characterization of these receptors and their role in many processes. In particular, dysiherbaine (DH) has been isolated from the Micronesian sponge *Dysidea herbacea* and has been found to be a potent kainate receptor agonist and subsequently, a powerful convulsant. (See Sakai et al., J. AM. CHEM. SOC. 1997; 119:4112-16; and Sakai et al., JPET 2001; 296:650-8, the contents of which are incorporate by reference in their entireties). Kainate receptor-selective epimeric analogs of dysiherbaine and the use thereof in pharmaceutical compositions and methods are disclosed in U.S. Published Application No. 2009-0118358, the content of which is incorporated by reference in its entirety.

NMDA receptors (NMDARs), another subgroup of the ionotropic glutamate receptor family, are a predominant physiological effector for synaptic plasticity and memory function. Activation of NMDARs results in the opening of an ion channel that is non-selective with respect to cations. NMDARs exhibit voltage-dependent activation as a result of $Mg^{2+}$ ions binding and blocking the ion channel. This allows voltage-dependent flow of $Na^+$ and small amounts of $Ca^{2+}$ ions into the cell and flow of $K^+$ ions out of the cell.

AMPA receptors (AMPARs), another subgroup of the ionotropic glutamate receptor family, also are responsible for excitatory neurotransmission in the mammalian central nervous system. Over-activation of AMPARs receptors contributes to the pathology of a number of neurological diseases, particularly epilepsy, neuropathic pain, and stroke. Preclinical data from animal models of these diseases support the potential therapeutic efficacy of inhibiting of AMPA receptors with selective antagonists. Several noncompetitive AMPA receptor antagonists are in clinical trials currently, but none have been approved by for use in humans yet. AMPAR receptor antagonism clearly is viewed as a viable, but not yet validated, therapeutic approach.

SUMMARY

Disclosed are compounds, pharmaceutical compositions, methods of treatment, and methods for selectively antagonizing a glutamate receptor, which may include ionotropic glutamate receptors iGluRs. In some embodiments, the disclosed compounds are utilized in pharmaceutical compositions, methods of treatment, and methods for selectively antagonizing an α-amino-3-hydroxyl-5-methyl-4-isoxazole-prpionate (AMPA) receptor, such as a receptor comprising one or more subunits including GluR1, GluR2, GluR3, and GluR4, including homomeric AMPA receptors (e.g., the GluR4 homomeric receptor) and heteromeric AMPA receptors (e.g., the GluR1/GluR2 heteromeric receptor). The disclosed compounds include biologically active glutamate analogues formed from a regioselective domino metathesis of 7-oxanorbornenes with electron-rich vinyl acetate.

In particular, the pharmaceutical compositions may include and the methods may utilize a compound having a formula ("Formula I"):

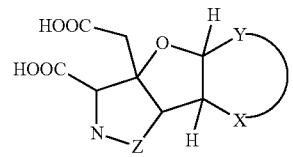

or a salt, ester, amide, or solvate thereof, wherein

X is —NH— or —O—;

Y is $C_3$-$C_4$-alkanediyl or $C_3$-$C_4$-alkenediyl, optionally substituted at one or more carbon positions with —OH; and Z is —$CH_2$— or —CO—.

Preferably, the compound has a formula ("Formula II"):

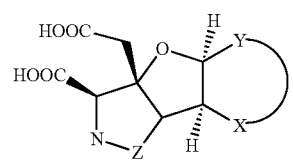

where X, Y, and Z are as defined above.

In some embodiments, X is —NH— and the compound has a formula ("Formula III"):

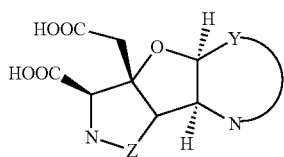

where Y and Z are as defined above. Preferably, the compound has a formula ("Formula IV"):

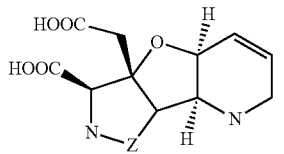

where Z is as defined above. Specific compounds include:

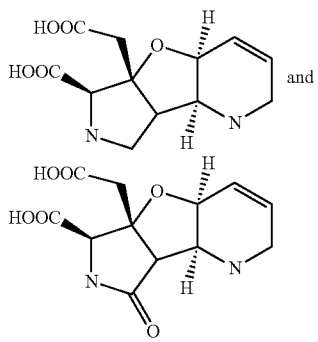

otherwise referred to as "IKM-27" and "IKM-159," respectively.

In other embodiments, X is —O— and the compound has a formula ("Formula V"):

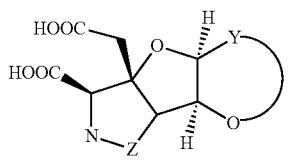

where Y and Z are as defined above. Preferably, Y is $C_3$-$C_4$-alkanediyl that is optionally substituted at one or more carbon positions with —OH; and Z is defined as above. Specific compounds include:

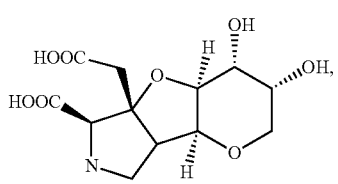

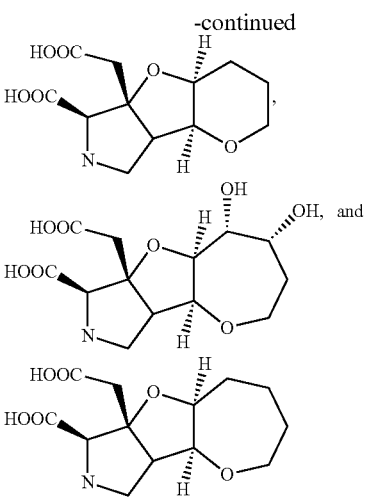

otherwise referred to as "IKM-86," "IKM-110," "IKM-107," and "IKM-98," respectively.

The pharmaceutical composition may be suitable for use in methods of treating or preventing neurological disorders or neurodegenerative diseases. The compounds may be utilized in treatment or preventive methods that include a step of selectively antagonizing one or more glutamate receptors such as ionotropic glutamate receptors, including, but not limited to, glutamate receptors comprising one or more subunits selected from GluR1, GluR2, GluR3, and GluR4. In some embodiments, the compounds may be utilized in treatment or preventive methods that include a step of selectively antagonizing a heteromeric GluR1/GluR2 receptor. In other embodiments, the compounds may be utilized in treatment or preventive methods that include a step of selectively antagonizing a homomeric GluR4 receptor.

DETAILED DESCRIPTION

Figure 1:
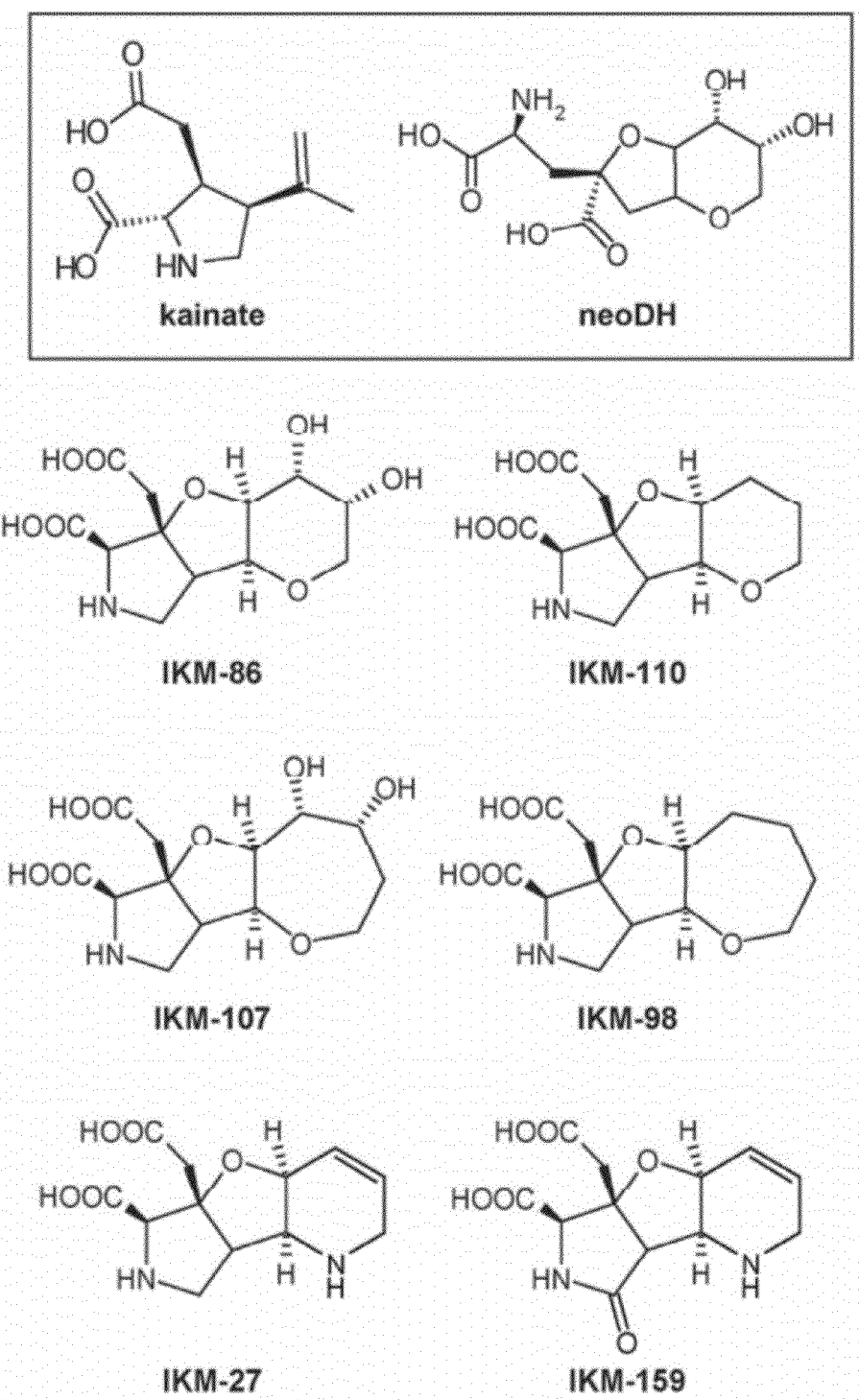
FIG. 1. Chemical structures of parent convulsants and synthetic IKM compounds.

Disclosed are heterotricyclic molecules (otherwise referred to as "IKM" analogs) that act pharmacologically as AMPA receptor antagonists. These molecules may be utilized as pharmacological tools, because of their unique subunit selectivity, or potentially as clinical agents or lead compounds for treatment of neurological diseases that have an imbalance in neuronal excitability as a central feature.

The molecules typically exhibit biological activity involving glutamate receptors. First, the molecules typically are subunit selective AMPA receptor antagonists. This means that they have the potential to act on a subset of receptors in the central nervous system (CNS), which could be advantageous in reducing unwanted side effects. Targeting of some, but not all, receptors with selective antagonists is recognized as an approach with potential utility in neurological diseases, but existing pharmacological agents do not have the requisite degree of selectivity to test this hypothesis. The disclosed IKM molecules could afford the first such opportunity. The disclosed IKM molecules also could serve as valuable pharmacological tools for the basic neuroscience community as a result of their specific activity. Second, the molecules exhibit a relatively weak affinity compared to other commonly used AMPA receptor antagonists. A global reduction in AMPA receptor activity is known to have detrimental consequences presumably because AMPA receptors are central to normal brain function. As such, the weak antagonism exhibited by the disclosed IKM molecules may be preferred over higher affinity ligands. Third, the disclosed IKM compounds act as CNS depressants in mice through mechanisms that may be ancillary to their AMPA receptor antagonism. If this is indeed the case, this combination of pharmacological actions (both of which would tend to dampen CNS excitation) could prove particularly useful in conditions of hyper-excitability like that observed in epilepsy.

DEFINITIONS

The disclosed subject matter further may be described utilizing terms as defined below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

The terms "patient" and "subject" may be used interchangeably herein. A patient may be a human patient. A patient may refer to a human patient having or at risk for acquiring a neurological disorder or a neurodegenerative disease.

As used herein, "iGluRs" refers to ionotropic glutamate receptors and "mGluRs" refers to metabotropic glutamate receptors. Ionotropic glutamate receptor further may be classified as "NMDA receptors" and "non-NMDA receptors." "NMDA receptors" refers to receptors for N-methyl-D-aspartic acid. The non-NMDA receptors include "AMPA receptors" and "KA receptors" (or kainate receptors).

As used herein, "AMPA receptors" refers to receptors for α-amino-3-hydroxy-5-methyl-4-isoxazolepropionic acid and includes receptors comprising one or more subunits selected from GluR1, GluR2, GluR3, and GluR4. "GluR1," "GluR2," "GluR3," and "GluR4" refer to AMPA glutamate receptor subtypes 1-4, respectively. An AMPA receptor may be "homomeric" (i.e., formed entirely of multiple molecules of a single subunit) or "heteromeric" (i.e., formed from multiple molecules of a mixture of subunits).

As used herein, "KA receptors" refers to receptors for kainic acid or salts thereof and includes the receptors GluR5, GluR6, GluR7, KA1, and KA2. As used herein, "GluR5," "GluR6," and "GluR7" refers to kainate glutamate receptor subtypes 5-7, respectively. "KA1 receptor" refers to kainic acid receptor subtype 1, and "KA2 receptor" refers to the kainic acid receptor subtype 2.

As used herein, "selectively antagonizing" is meant to include antagonism resulting from selective binding of the disclosed compounds to a receptor comprising one or more subunits selected from a group consisting of GluR1, GluR2, GluR3, or GluR4 subunits, relative to non-AMPA receptors (e.g., relative to a receptor comprising one or more subunits selected from GluR5, GluR6, GluR7, KA1, and KA2; or relative to a NMDA receptor). For example, the compound may have a binding affinity for GluR1 receptor, GluR2 receptor, GluR3 receptor, GluR4 receptor (or a binding affinity for a receptor comprising one or more subunits selected from a group consisting of GluR1, GluR2, GluR3, or GluR4 subunits where the receptor is formed from a mixture of one or more subunits such as a heteromeric GluR1/GluR2 receptor) that is at least 3-fold greater (or at least 5-fold greater, at least 10-fold greater, at least 20-fold greater, at least 50-fold greater, or at least 100-fold greater) than a binding affinity for a non-AMPA receptors (e.g., than a binding affinity for any of the receptors GluR5, GluR6, GluR7, KA1, and KA2 or than a binding affinity for a glutamate receptor that does not comprise any of GluR1, GluR2, GluR3, and GluR4 subunits).

Optionally, the compound may displace AMPA. (e.g., [$^3$H]-AMPA) from AMPA receptors (i.e., a receptor comprising one or more subunits selected from a group consisting of GluR1, GluR2, GluR3, and GluR4 subunits) more efficiently than from non-AMPA receptors (e.g., a receptor comprising one or more subunits selected from a group consisting of GluR5, GluR6, GluR7, KA1, and KA2). In some embodiments, a selective antagonist may have a $K_i$ value ($K_i=IC_{50}/(1+[radioligand]/K_d)$ for a receptor comprising one or more subunits selected from GluR1, GluR2, GluR3, and GluR4, which is less than about 100 μM (preferably less than about 50 μM, more preferably less than about 30 μM, even more preferably less than about 20 μM, and most preferably less than about 10 μM); and the selective antagonist may have a $K_i$ value for a non-NMDA receptor (e.g., a receptor comprising one or more subunits selected from a group consisting of GluR5, GluR6, GluR7, KA1, and KA2) that is greater than about 50 μM, (preferably greater than about 70 μM, more preferably greater than about 80 μM, even more preferably greater than about 90 μM, and most preferably greater than about 100 μM). For example, a selective antagonist for a receptor comprising one or more subunits selected from GluR1, GluR2, GluR3, and GluR4 may have: (i) a $K_1$ value for a GluR1/GluR2 heteromeric receptor or a GluR4 homomeric receptor of less than about 100 μM; and (ii) a $K_i$ value for a receptor comprising one or more subunits selected from GluR5, GluR6, GluR7, KA1, KA2, and an NMDA which is greater than about 100 μM.

Compounds for the pharmaceutical compositions and methods disclosed herein include glutamate analogues. Glutamate analogues, as contemplated herein, include, but are not limited to, compounds having Formula I

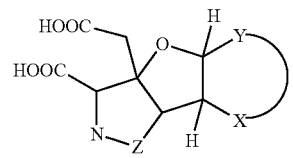

or a salt, ester, amide, or solvate thereof, wherein

X is —NH— or —O—;

Y is $C_3$-$C_4$-alkanediyl or $C_3$-$C_4$-alkenediyl, optionally substituted at one or more carbon positions with —OH; and Z is —CH$_2$— or —CO—. The disclosed compounds may include heterotricyclic AMPA receptor antagonist.

The compounds disclosed herein can be prepared, for example, using the synthetic scheme described in Ikoma et al., "Regioselective Domino Methathesis of 7-Oxanorbornenes and Its Application to the Synthesis of Biologically Active Glutamate Analogues," *Eur. J. Org. Chem.* 2008, 5215-5220; and Oikawa et al., "Regioselective Domino Metathesis of Unsymmetrical 7-Oxanorbornenes with Electron-rich Vinyl Acetate toward Biologically Active Glutamate Analogues," *Eur. J. Org. Chem.*, 2009, 5531-5548; which are hereby incorporated by reference in their entireties It will be appreciated that the compounds disclosed herein (e.g., compounds of Formulas I, II, III, IV, and V) may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers of the disclosed glutamate analogue compounds are contemplated herein (e.g., a composition comprising at least about 90%, 95%, or 99% pure stereoisomer, epimer, or enantiomer such as any of the compounds referred to as IKM-86, IKM-110, IKM-107, IKM-98, IKM-27, and IKM-159.)

As used herein, formulae which do not specify the orientation at one or more chiral centers are meant to encompass all orientations and mixtures thereof. Illustratively, the compounds of Formula I:

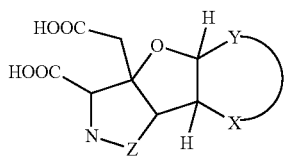

are meant to include, but are not limited to, compounds having the following formulae:

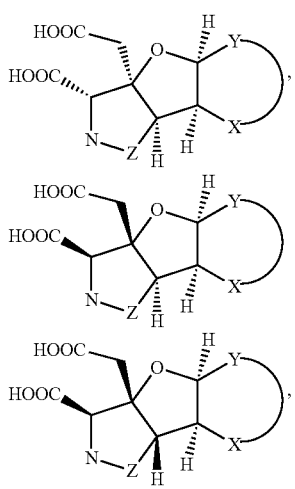

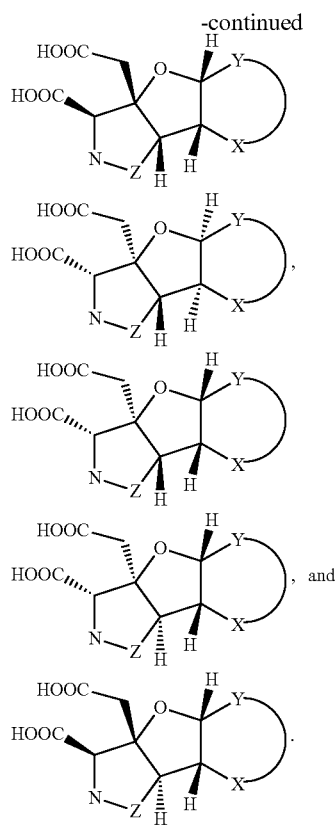

Compounds of Formula I are meant to include, but are not limited to, the compounds referred to as IKM-86, IKM-110, IKM-107, IKM-98, IKM-27, and IKM-159.

As indicated above, pharmaceutically acceptable salts of the compounds are contemplated and also may be utilized in the disclosed methods. For example, the carboxylic acid groups of the disclosed compounds may be deprotonated and the amino groups of the disclosed compounds may be protonated. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

It should be recognized that the particular counter-ion forming a part of any salt of a compound disclosed herein is usually not of a critical nature, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

It will be further appreciated that the disclosed compounds can be in equilibrium with various inner salts, such as those represented by, but not limited to, the following formulae:

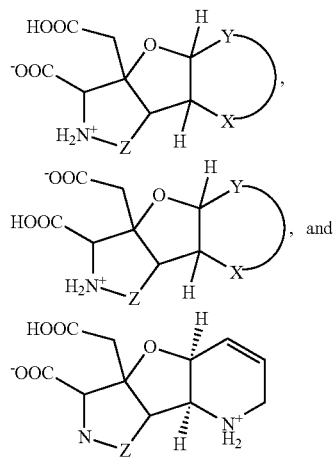

where X and Y are as defined above, and that all of these and other inner salts are meant to be encompassed by the disclosed compounds and formulae.

The methods disclosed herein may be practiced in vitro or in vivo. More particularly, the methods disclosed herein may be used in vivo to treat neuropathic pain and other forms of aberrant nociception as well as migraines, epilepsy, and other neurological disorders. In the case where the methods disclosed herein are carried out in vivo, for example, where the GluR1 receptor, GluR2 receptor, GluR3 receptor, or GluR4 receptor (or a receptor comprising one or more subunits selected from GluR1, GluR2, GluR3, and GluR4 subunits, for example, a heteromeric GluR1/GluR2 receptor) are present in a human subject, contacting can be carried out by administering a therapeutically effective amount of the compound to the human subject. For example, the compound may be directly injected into the subject in the vicinity of a GluR1 receptor, GluR2 receptor, GluR3 receptor, or a GluR4 receptor (or a receptor comprising one or more subunits selected from GluR1, GluR2, GluR3, and GluR4 subunits, for example, a heteromeric GluR1/GluR2 receptor), or the compound may be introduced into the subject by other suitable means of administration. Details with regard to this and other methods for administering compounds in accordance with the methods disclosed herein are further described below.

Also disclosed are methods of treating a neurological disorder or a neurodegenerative disease in a subject. The methods may include administering to the subject a glutamate analogue as contemplated herein that is a selective antagonist for a GluR1 receptor, GluR2 receptor, GluR3 receptor, or GluR4 receptor (or a receptor comprising one or more subunits selected from GluR1, GluR2, GluR3, and GluR4 subunits, for example, a heteromeric GluR1/GluR2 receptor).

As used herein, a "glutamate analogue that is a selective antagonist" refers to a compound that is both: (i) a glutamate analogue as contemplated herein; and (ii) a selective antagonist (e.g., a selective antagonist for an AMPA receptor). A selective antagonist for an AMPA receptor may include an antagonist that is selective for a GluR1 receptor, a GluR2 receptor, a GluR3 receptor, or a GluR4 receptor (or that is selective for a heteromeric receptor such as GluR1/GluR2), relative to a kainate receptor or other non-AMPA receptor such as an NMDA receptor. The terms "selective GluR1 receptor antagonist," "selective GluR2 receptor antagonist," "selective GluR3 receptor antagonist," and "selective GluR4 receptor antagonist" are meant to refer to those compounds which selectively bind to a GluR1 receptor, a GluR2 receptor, a GluR3 receptor, and a GluR4 receptor, respectively, relative to kainate receptors (e.g., relative to the GluR5, GluR6, GluR7, KA1, and KA2 receptors), or relative to other non-AMPA receptors (e.g., relative to NMDA receptors or metabotropic glutamate receptors). The term "selective GluR1/GluR2 receptor antagonist" refers to those compounds which selectively bind to a heteromeric GluR1/GluR2 receptor relative to kainate receptors (e.g., relative to the GluR5, GluR6, GluR7, KA1, and KA2 receptors), or relative to other non-AMPA receptors (e.g., relative to NMDA receptors or metabotropic glutamate receptors)

Examples of compounds have been discussed hereinabove, and all such examples of compounds can be used in the treatment methods disclosed herein. Illustratively, the treatment methods disclosed herein may be practiced using a selective glutamate analogue having any of Formulae I-V.

The disclosed compounds may be used to prepare pharmaceutical compositions for administering in methods of treating a "neurological disorder or a neurodegenerative disease." As used herein, "neurological disorder or neurodegenerative disease" is meant to include neuropathic pain and other forms of aberrant nociception as well as migraines, epilepsy, and other neurological disorders. Examples of such neurological disorders or neurodegenerative diseases include, but are not limited to, Alzheimer's Disease; Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; post-traumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; and post-traumatic pain.

As used herein, the term "migraine" refers a disorder of the nervous system characterized by recurrent attacks of head pain (which are not caused by a structural brain abnormality such as those resulting from tumor or stroke), gastrointestinal disturbances, and possibly neurological symptoms such as visual distortion. Characteristic headaches of migraine usually last one day and are commonly accompanied by nausea, emesis, and photophobia. Migraine can be a "chronic" condition. The term "chronic," as used herein, means a condition of slow progress and long continuance. As such, a chronic condition can be treated when it is diagnosed, and treatment can be continued throughout the course of the disease. Conversely, the term "acute" means an exacerbated event or attack, of short course, followed by a period of remission. Thus, the treatment of migraine contemplates both acute events and chronic conditions. In an acute event, the aforementioned compounds can be administered at the onset of symptoms and discontinued when the symptoms disappear. As described above, a chronic condition can be treated throughout the course of the disease.

Suitable subjects include, for example mammals, such as rats, mice, cats, dogs, monkeys, and humans. Suitable human subjects include, for example, those who have or who have previously been determined to be at risk for developing Alzheimer's Disease; Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; post-traumatic stress syndrome; tardive dyskinesia; psychosis related to depression, schizophrenia, bipolar disorder, mania, and drug intoxication or addiction; acute or chronic pain states; migraine; severe pain, intractable pain; neuropathic pain; and/or post-traumatic pain. Other suitable human subjects include, for example, those who have been diagnosed as having Alzheimer's Disease; Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; posttraumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; post-traumatic pain; and/or cancer (e.g., glioblastoma). Still other suitable human subjects include, for example, those who have not been diagnosed as having and/or who have not previously been determined to be at risk of having or developing one or more of the following: Alzheimer's Disease; Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; post-traumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; post-traumatic pain; and/or cancer (e.g., glioblastoma).

As used herein, the terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the individual.

As used herein, the terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to an individual at risk of developing a particular disease, to an individual reporting one or more of the physiological symptoms of a disease, or to an individual at risk of reoccurrence of the disease.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with GluR1 receptor activity, GluR2 receptor activity, GluR3 receptor activity, or GluR4 receptor activity (or receptor activity of a receptor comprising mixed subunits selected from GluR1, GluR2, GluR3, and GluR4 subunits, for example, activity of a heteromeric GluR1/GluR2 receptor). The disclosed methods may include administering an effective amount of the disclosed compounds (e.g., as present in a pharmaceutical composition) for treating a neurological disorder or neurodegenerative disease.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the neurological disorder or neurodegenerative disease involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

The selective GluR1 receptor antagonists, GluR2 receptor antagonists, GluR3 receptor antagonists, and GluR4 receptor antagonists for use according to the methods of disclosed herein may be a single compound or a combination of compounds. For example, the methods disclosed herein may be practiced using a composition containing a single receptor antagonist, or it can be practiced using a composition containing two or more receptor antagonists, which may be the same or different compounds. For example, the methods disclosed herein may be practiced using a composition containing a mixture of compounds that are selective for one or more of a GluR1 receptor, a GluR2 receptor, a GluR3 receptor, and a GluR4 receptor (or a receptor comprising one or more subunits selected from GluR1, GluR2, GluR3, and GluR4, for example, a heteromeric GluR1/GluR2 receptor). The aforementioned compositions may optionally contain one or more other active agents such as those disclosed in U.S. Pat. No. 6,759,418 to Filla et al., which is hereby incorporated by reference; WO 98/45270, which is hereby incorporated by reference; and U.S. Published Application No. 2009-0118358, which is hereby incorporated by reference. For example, additionally or alternatively, the aforementioned compositions can optionally contain one or more non-selective selective GluR1 receptor antagonists, GluR2 receptor antagonists, GluR3 receptor antagonists, or GluR4 receptor antagonists (i.e., a compound that is an antagonist of one or more glutamate receptors other than GluR1 receptor, GluR2 receptor, GluR3 receptor, or GluR4 receptor); or the aforementioned compositions can be substantially free of non-selective GluR1 receptor antagonists, GluR2 receptor antagonists, GluR3 receptor antagonists, and GluR4 receptor antagonists. Still additionally or alternatively, the aforementioned compositions can optionally contain one or more compounds capable of blocking activity at one or more other glutamate receptors, including metabotropic glutamate receptors and ionotropic glutamate receptors (e.g., GluR5 receptors, GluR6 receptors, GluR7 receptors, KA-1 receptors, KA-2 receptors, or other kainate receptors; NMDA receptors; and non-NMDA receptors); or the aforementioned compositions can be substantially free of compounds capable of blocking activity at one or more other glutamate receptors (e.g., GluR5 receptors, GluR6 receptors, GluR7 receptors, KA-1 receptors, KA-2 receptors, or other kainate receptors; NMDA receptors; and non-NMDA receptors).

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

As one skilled in the art will also appreciate, the formulation can be prepared with materials (e.g., actives excipients, carriers, diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The following list of formulations is illustrative. These illustrative formulations may be suitable for preparing pharmaceutical compositions that include the disclosed glutamate analogues (e.g., heterotricyclic AMPA receptor antagonists) as "active ingredients." The following list of formulations is illustrative and should not be interpreted as limiting the present disclosure or claims in any way:

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules, each containing 80 mg medicament, are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| Active Ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8
An intravenous formulation containing 100 mg of medicament per 5 ml dose can be prepared as follows:

| Active Ingredient | 100 mg |
|---|---|
| Mannitol | 100 mg |
| 5N Sodium hydroxide | 200 ml |
| Purified water to total | 5 ml |

ILLUSTRATIVE EMBODIMENTS

The following embodiments are illustrative and are not intended to limit the disclosed subject matter.

Embodiment 1

A pharmaceutical composition comprising: (a) a compound having a formula:

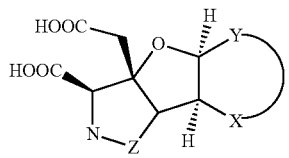

or a salt, ester, amide, or solvate thereof, wherein X is —NH— or —O—; Y is $C_3$-$C_4$-alkanediyl or $C_3$-$C_4$-alkenediyl, optionally substituted at one or more carbon positions with —OH; and Z is —CH$_2$— or —CO—; and (b) one or more pharmaceutically acceptable carriers, diluents, or excipients.

Embodiment 2

The composition of embodiment 1, wherein the compound has a formula:

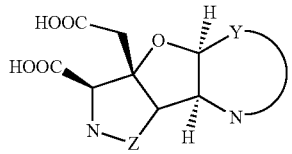

Embodiment 3

The composition of embodiment 2 wherein the compound has a formula:

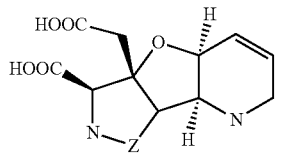

Embodiment 4

The composition of embodiment 3 wherein the compound has a formula:

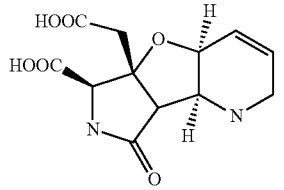 [SMILES: O=C(O)C[C@@]12O[C@H]3C=CCN[C@H]3C1C(=O)N[C@H]2C(=O)O]

Embodiment 5

The composition of embodiment 3 wherein the compound has a formula:

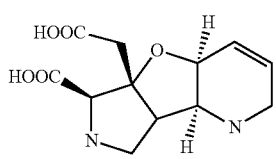

Embodiment 6

The composition of embodiment 1 wherein the compound as a formula:

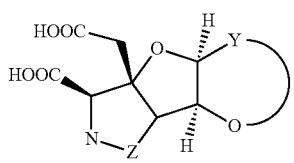

Embodiment 7

The composition of embodiment 6 wherein the compound has a formula:

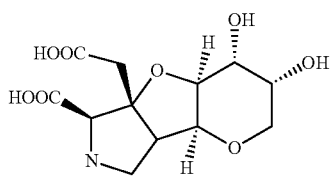 [SMILES: O=C(O)C[C@@]12O[C@H]3[C@H](O)[C@H](O)CO[C@H]3C1CN[C@H]2C(=O)O]

Embodiment 8

The composition of embodiment 6 wherein the compound has a formula:

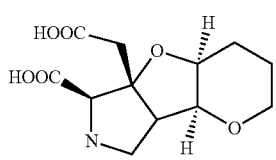

Embodiment 9

The composition of embodiment 6 wherein the compound has a formula:

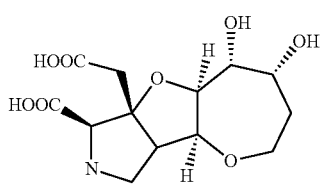 [SMILES: O=C(O)C[C@@]12O[C@H]3[C@H](O)[C@H](O)CCO[C@H]3C1CN[C@H]2C(=O)O]

Embodiment 10

The composition of embodiment 6 wherein the compound has a formula:

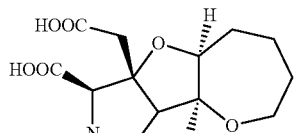

Embodiment 11

The composition of any of embodiments 1-10, wherein the compound has an $IC_{50}$ for a receptor comprising one or more subunits selected from GluR1, GluR2, GluR3, and GluR4 of less than about 100 µM.

Embodiment 12

The compound of embodiment 11, wherein the receptor is a heteromeric GluR1/GluR2 receptor.

Embodiment 13

The compound of embodiment 11, wherein the receptor is a homomeric GluR4 receptor.

Embodiment 14

The composition of any of embodiments 1-13, wherein the composition is suitable for administration to a human.

Embodiment 15

The composition of any of embodiments 1-13, wherein the composition is suitable for oral administration.

Embodiment 16

The composition of any of embodiments 1-13, wherein the composition is suitable for transdermal administration.

Embodiment 17

The composition of any of embodiments 1-16, wherein the composition comprises an effective amount of the compound for treating a neurological disorder or neurodegenerative diseases selected from the group consisting of Alzheimer's Disease, Huntington's Chorea; inherited ataxias; AIDS-induced dementia; amyotrophic lateral sclerosis; idiopathic and drug-induced Parkinson's Disease; ocular damage; retinopathy; muscular spasticity; tremors; drug tolerance and withdrawal; brain edema; convulsive disorders; epilepsy; depression; anxiety; post-traumatic stress syndrome; tardive dyskinesia; psychosis related to depression, schizophrenia, bipolar disorder, mania, and drug intoxication or addiction; acute or chronic pain states; migraine; severe pain; intractable pain; neuropathic pain; and post-traumatic pain.

Embodiment 18

A method of treating a neurological disorder or a neurodegenerative disease in a subject, the method comprising administering to the subject the pharmaceutical composition of any of embodiments 1-17.

Embodiment 19

A method for selectively antagonizing a glutamate receptor, the method comprising contacting the receptor with a compound having a formula:

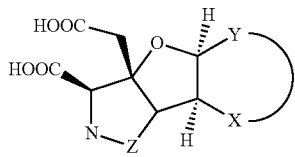

or a salt, ester, amide, or solvate thereof, wherein X is —NH— or —O—; Y is $C_3$-$C_4$-alkanediyl or $C_3$-$C_4$-alkenediyl that is optionally substituted at one or more carbon positions with —OH; and Z is —$CH_2$— or —CO—.

Embodiment 20

The method of embodiment 19 wherein the compound has a formula:

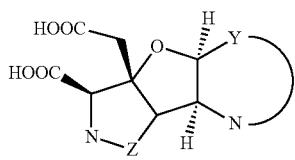

Embodiment 21

The method of embodiment 20 wherein the compound has a formula:

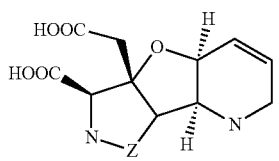

Embodiment 22

The method of embodiment 21 wherein the compound has a formula:

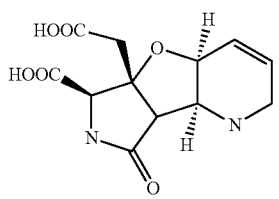 [SMILES: O=C(O)C[C@@]12O[C@H]3C=CCN[C@H]3C1C(=O)N[C@H]2C(=O)O]

Embodiment 23

The method of embodiment 21 wherein the compound has a formula:

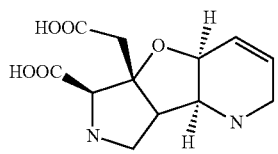 [SMILES: O=C(O)C[C@@]12O[C@H]3C=CCN[C@H]3C1CN[C@H]2C(=O)O]

Embodiment 24

The method of embodiment 19 wherein the compound as a formula:

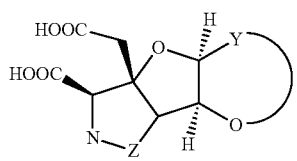

Embodiment 25

The method of embodiment 24 wherein the compound has a formula:

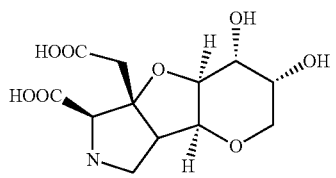 [SMILES: O=C(O)C[C@@]12O[C@H]3[C@H](O)[C@H](O)CO[C@H]3C1CN[C@H]2C(=O)O]

Embodiment 26

The method of embodiment 24 wherein the compound has a formula:

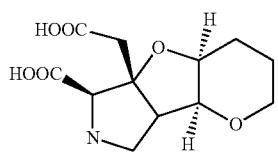 [SMILES: O=C(O)C[C@@]12O[C@H]3CCCO[C@H]3C1CN[C@H]2C(=O)O]

Embodiment 27

The method of embodiment 24 wherein the compound has a formula:

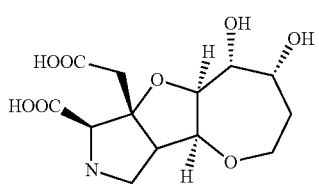 [SMILES: O=C(O)C[C@@]12O[C@H]3[C@H](O)[C@H](O)CCO[C@H]3C1CN[C@H]2C(=O)O]

Embodiment 28

The method of embodiment 24 wherein the compound has a formula:

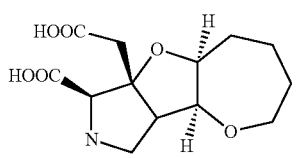 [SMILES: O=C(O)C[C@@]12O[C@H]3CCCCO[C@H]3C1CN[C@H]2C(=O)O]

Embodiment 29

The method of embodiment 19, wherein the contacting is performed in vivo.

Embodiment 30

The method of any of embodiments 19-29, wherein the glutamate receptor is an ionotropic glutamate receptor.

Embodiment 31

The method of any of embodiments 19-29, wherein the glutamate receptor is a receptor comprising one or more subunits selected from GluR1, GluR2, GluR3, and GluR4.

Embodiment 32

The method of any of embodiments 19-29, wherein the receptor is a heteromeric GluR1/GluR2 receptor.

Embodiment 33

The method of any of embodiments 19-29, wherein the receptor is a homomeric GluR4 receptor.

Embodiment 34

The method of embodiment 19, wherein the receptor is contacted with an effective concentration of the compound for selectively antagonizing the receptor.

EXAMPLE

The following example is illustrative and is not intended to limit the disclosed subject matter. Reference is made to Gill et al., "A series of structurally novel heterotricyclic AMPA receptor-selective antagonists," Br. J. Pharmacol. 2010 July; 160(6): 1417-29, the content of which is incorporated herein by reference in its entirety.

Abstract

A new class of heterotricyclic glutamate analogues recently was generated by incorporating structural elements of two excitotoxic marine compounds, kainic acid (KA) and neodysiherbaine A (neoDH). Rather than acting as convulsants, several of these "IKM" compounds markedly depressed CNS activity in mice. Here, the pharmacological profile of these IKM compounds was generated with a focus on the most potent of these molecules, IKM-159.

The pharmacological activity and specificity of IKM compounds was characterized using whole-cell patch clamp recording from neurons and heterologous receptor expression systems, in combination with radioligand binding techniques. The majority of the IKM compounds tested reduced excitatory synaptic transmission in neuronal cultures, and IKM-159 inhibited synaptic currents from CA1 pyramidal neurons in hippocampal slices. IKM-159 inhibited glutamate-evoked whole cell currents from recombinant GluA2 and GluA4-containing AMPA receptors most potently, whereas kainate and NMDA receptor currents were not reduced by IKM-159. Antagonism of steady-state currents was agonist concentration-dependent, suggesting that its mechanism of action was competitive, although it paradoxically did not displace [$^3$H]-AMPA from receptor binding sites. IKM-159 reduced spontaneous action potential firing in both cultured hippocampal neurons in control conditions and during hyperactive states in an in vitro model of status epilepticus. Accordingly, IKM-159 was shown to be an AMPA receptor selective antagonist. IKM-159 and related nitrogen heterocycles represent structurally novel AMPA receptor antagonists with accessible synthetic pathways and potentially unique pharmacology, which could be of use in exploring the role of specific populations of receptors in neurophysiological and neuropathological processes.

Introduction

Physiological brain function relies on a delicate balance of excitatory and inhibitory neurotransmission acting on the dynamic intrinsic excitability of neurons (Nelson et al., 2008; Nelson et al., 1998). Excitatory synaptic transmission is critically mediated by ionotropic glutamate receptors (iGluRs). Three sub-families of receptors comprise the iGluRs-N-methyl-D-aspartate (NMDA), α-amino-3-hydroxyl-5-methyl-4-isoxazole-propionate (AMPA) and kainate (KA) receptors (Hollmann et al., 1994; Mayer et al., 1987). Disruption of the delicate balance between these excitatory receptors and their inhibitory counterparts contributes to many CNS injury and disease states, particularly epilepsy (Ben-Ari, 2001; Jensen, 2002).

Antagonists acting on all three iGluR subtypes are efficacious in a variety of laboratory models of disease (Gigler et al., 2007; Namba et al., 1994; O'Neill et al., 1998; Smith et al., 2000), but very few successful outcomes have been achieved in clinical trials with these molecules (e.g., Hoyte et al., 2004; Walters et al., 2005; Wood, 2005). Currently, only one iGluR antagonist is used clinically, the rapidly dissociating uncompetitive NMDA receptor antagonist, memantine (Parsons et al., 2007), although selective antagonists of NMDA receptors containing the GluN2B subunit are in clinical studies (Gogas, 2006; Mony et al., 2009). The generation of molecules with enhanced pharmacological specificity for a subset of iGluRs in the brain therefore represents a promising treatment strategy that remains largely unexplored, particularly with respect to AMPA receptors.

Current rational drug design to generate new pharmacological and clinical tools within small molecule libraries employs several synthesis paradigms, including diversity-oriented synthesis (DOS), which typically produces a structurally complex and diverse library that is screened for activity on a variety of molecular targets (Cordier et al., 2008; Tan, 2005). Recently, a modest DOS approach was utilized in order to create a family of novel heterocyclic scaffolds referred to as "IKM" compounds (Ikoma et al., 2008; Oikawa et al., 2009). The IKM molecules were inspired by two naturally occurring convulsants, kainic acid (KA) and neodysiherbaine A (neoDH), which are potent glutamate receptor agonists (Swanson et al., 2009). Despite their structural resemblance to KA and neoDH, however, several of the IKM molecules elicited pronounced hypoactivity and muscle rigidity characteristic of catalepsy, instead of seizure behaviors, in preliminary in vivo mouse bioassays (Ikoma et al., 2008; Oikawa et al., 2009).

In the current study, the pharmacological activity underlying this apparent depression of CNS function was studied. The majority of the IKM compounds reduced synaptic excitation and excitability in cultured hippocampal neurons through antagonism of neuronal AMPA receptors. The most potent molecule in behavioral studies, IKM-159, inhibited AMPA receptors but did not alter kainate or NMDA receptor currents. Action potential firing in in vitro basal and seizure-like states was reduced in the presence of the IKM compounds, which may in part underlie their in vivo behavioral properties. IKM-159 therefore could serve as a template for a series of more potent AMPA receptor-selective antagonists with greater therapeutic potential.

Experimental Procedures

Receptor Nomenclature. Receptor nomenclature conforms to the British Journal of Pharmacology's Guide to Receptors and Channels (BrJPharm GRAC) (Alexander et al., 2008). Splice variants, where appropriate, were designated after the BrJPhann GRAC nomenclature.

Reagents and plasmids. All salts, buffers, potassium channel antagonists, tetraethylammonium chloride (TEA; T2265), 4-aminopyridine (4-AP; 275875), and lidocaine M-ethyl bromide (QX-314; L5783) were purchased from Sigma-Aldrich (Saint Louis, Mo.) Kynureic acid (0223), D-O-2-amino-5-phosphonopentanoic acid (D-APV; 0106), DL-2-amino-5-phosphonopentanoic acid (D,L-APV; 0105), 6-cyano-7-nitroquinoxaline-2,3-dione (CNQX; 0190), picrotoxin (PTX; 1128), and bicuculline methiodide (Bic; 2503] were purchased from Tocris Bioscience (Ellisville, Mo.). Rat GluA1-4 flip cDNAs within the pRK plasmids were provided by Peter Seeburg (University of Heidelberg, Germany), while myc-tagged rat GluK1-2b and GluK2a cDNAs within pcDNA3.1 plasmids were provided by John Marshall (Brown University) and Christophe Mulle (Université Bordeaux II, France).

Cell Culture and Transfection. Human embryonic kidney cells expressing T-antigen, clone 17 (HEK293-T/17) (CRL-11268) were cultured at 37° C. with 5% $CO_2$ in DMEM, including 100 μg/mL penicillin, 100 μg/mL streptomycin, and 10% heat-inactivated fetal bovine serum. Cells were split twice per week. For transfection, HEK293-T/17 cells were plated at $3 \times 10^4$ cells/cm² for pharmacology experiments and $5 \times 10^3$ cells/cm² for physiology experiments in fresh medium 24 h prior to transfection. Cells were transfected with AMPA or KA receptor plasmid cDNAs using Mirus Trans-IT transfection reagent (Minus Bio Corporation, Madison, Wis.) at a ratio of 1 μg cDNA: 3 μL Trans-1T reagent and maintained in transfection medium overnight followed by a media change the next day. Transfected cells were maintained in this medium until the experiment was conducted (48-72 h total post transfection).

Electrophysiology. For analysis of recombinant receptors, HEK293-T/17 cells were co-transfected with 0.2 μg of iGluR cDNA and 0.05 μg of eGFP. For heterologous GluA1/GluA2 receptors, the GluA1:GluA2 cDNA ratio was 1:6. Two to three days post-transfection, eGFP-expressing cells were lifted from the cover slip and voltage clamped in whole cell mode. The internal solution contained (in mM) 30 CsF, 110 CsCl, 10 HEPES, 4 NaCl, 5 EGTA and 0.5 $CaCl_2$ (pH 7.3), while the extracellular solution contained (in mM) 140 NaCl, 10 glucose, 10 Cs-HEPES, 3 KCl, 2 $CaCl_2$ and 1 $MgCl_2$ (pH 7.3). Borosilicate patch electrodes were pulled and fire polished to 2-3 MO resistance. Lifted cells were maintained in a laminar stream of extracellular solution from a triple-barreled flow pipe, which was rapidly translated using a piezoceramic bimorph for fast application of glutamate or kainate alone or in combination with various antagonists (the 10-90% rise time of glutamate-evoked currents was ~1 ms). IKM compounds were applied for three minutes with analysis performed on the final one minute of drug application.

Experiments involving primary hippocampal neurons were carried out as described previously (Vivithanaporn et al., 2007). Dissociated neurons were cultured from E18 prenatal hippocampi and were used for analysis from between 17 and 28 days in vitro. The extracellular solution was the same as used for recombinant receptor analysis, while the internal solution for voltage clamp recordings contained (in mM) 95 CsF, 25 CsCl, 10 Cs-HEPES, 10 EGTA, 2 NaCl, 2 Mg-ATP, 10 QX-314, 5 TEA. and 5 4-AP (pH 7.3) and the internal solution for current clamp recordings contained (in mM) 120 $KMeSO_4$, 5 KCl, 5 NaCl, 1 $MgCl_2$, 11 Na-HEPES, 10 phosphocreatine, 4 Na-ATP, and 0.3 Na-GTP (pH 7.0). Borosilicate patch electrodes were pulled and fire polished to 3-5 MΩ resistance. Both whole cell current clamp and voltage clamp recordings were performed using an Axopatch 200B amplifier (MDS, Sunnyvale, Calif.) and filtered at 20 kHz. Gigaohm seals were established in voltage clamp mode and, after membrane rupture, the recordings were carried out either in voltage clamp (clamped at $V_m=-70$ mV) with a 5-15 mΩ series resistance, which was compensated to ~60%, or in current clamp mode ($V_m=60-65$ mV) with the bridge balance was corrected and pipette resistance neutralized. In vitro status epilepticus (SE) was induced as described previously (Deshpande et al., 2007; Pal et al., 1999) and action potentials were recorded in current clamp mode. Briefly for in vitro SE, magnesium-containing external solution was exchanged for external solution without magnesium and supplemented with 2 μM glycine. This solution exchange produced a period of rapid depolarization and increased AP firing, followed by a period of channel inactivation and reduced AP firing. After channel inactivation, neurons characteristically would hyperpolarize to hold at a membrane voltage ($V_m$) which was depolarized relative to control $V_m$, with an increase in AP firing frequency. Neurons were excluded from analysis if the AP firing frequency after the period after channel inactivation did not hold at ~2 Hz for at least two minutes or demonstrated a significant rundown in AP firing frequency prior to administration of experimental compounds. External solutions were bath-applied at a flow rate of 1.5-2 ml/minute. After recording a basal control period, IKM compounds were applied for five minutes (10 minutes for in vitro SE experiments) and changes in excitatory post-synaptic current (EPSC) charge transfer or action potential (AP) frequency were analyzed during the last two minutes of IKM application.

For recordings from acute hippocampal slices, brains from P15-21 C57Bl/6 mice were sliced transversely (350 μm thickness) in a sucrose slicing solution containing (in mM) 85 NaCl, 2.5 KCl, 1.25 $NaH_2PO_4$, 25 $NaHCO_3$, 25 glucose, 75 sucrose, 0.5 $CaCl_2$, 4 $MgCl_2$, 0.5 Na ascorbate, 10 μM DL-APV and 100 μM kynurenic acid (pH 7.3). After slicing, the solution was exchanged with an incubation solution containing (in mM) 125 NaCl, 2.4 KCl, 1.2 $NaH_2PO_4$, 25 $NaHCO_3$, 25 glucose: 1 CaCl$_2$, 2 MgCl$_2$, 0.5 Na ascorbate, 10 µM DL-APV and 100 µM kynurenic acid (pH 7.3) that was bubbled continuously with CO$_2$-balanced O$_2$ (carbogen). During this solution exchange, the temperature of the bath was slowly increased to 32° C. and then allowed to return to ~23° C., after which slices were transferred to the recording bath for experiments. Recordings in voltage clamp mode used the CsF/CsCl internal solution and carbogenated external recording solution containing (in mM) 120 NaCl, 2.4 KCl, 2 MgCl$_2$, 1 CaCl$_2$, 25 NaHCO$_3$, 1.2 NaH$_2$PO$_4$, 25 glucose, 10 µM bicuculline methiodide, 50 µM PTX and 50 µM D-APV (pH 7.3). For NMDA EPSCs, MgCl$_2$ was omitted and glycine (10 µM)/CNQX (50 µM) added to the external solution. NMDA EPSCs were validated by addition of D-APV (50 µM) at the end of each recording. Hippocampal CA1 or CA3 pyramidal cells were voltage clamped at −70 mV and stimulated with a monopolar electrode either the stratum radiatum or *stratum lucidum*, respectively. IKM compounds were applied for 10 minutes and changes in the peak amplitudes of excitatory post-synaptic currents (EPSCs) and paired-pulse ratios were analyzed during the last two minutes of drug application. EPSC charge transfer, AP frequency, paired-pulse ratio and EPSC peak amplitude were analyzed with Mini-Analysis v6.03 (Synaptosoft, Decatur, Ga.) and Clampfit v10.0 (MDS, Sunnyvale, Calif.) software.

Radioligand binding. HEK293-T/17 cells were transfected with 5 µg of iGluR cDNA in 100 mm$^2$ culture dishes. Two days post transfection, the plates were washed twice with ice-cold Dulbecco's phosphate-buffered saline (DPBS) and then incubated with 50 mM Tris (pH 7.4) and 1 mM EDTA for three minutes on ice. Cells were collected and centrifuged for five minutes at 800 g at room temperature. The cell pellet was homogenized in 50 mM Tris (pH 7.4) containing 320 mM sucrose (homogenization buffer, HB) on ice using a glass dounce homogenizer and centrifuged at 4° C. for 10 minutes at 800 g. The supernatant, containing the membrane fragments, was saved and the remaining pellet containing nuclei and unbroken cells was resuspended in HB. This homogenization process was repeated two more times and after collection of the final resulting supernatant, the remaining pellet was discarded. The collected supernatants were centrifuged at 4° C. for 20 minutes at 20000 g and the resulting supernatant was discarded leaving a membrane-containing pellet. The pellets were resuspended in freshly prepared binding buffer containing (in mM) 50 Tris (pH 7.2), 2.5 CaCl$_2$, 10% glycerol and 100 KSCN (for AMPA receptors) or exclusively 50 Tris (pH 7.4) (for kainate receptors). Membrane protein (50-100 µg) was combined with radiolabeled ligand (10 nM [$^3$H]-KA or 20 nM [$^3$H]-AMPA for kainate receptor and AMPA receptor binding, respectively), alone or with 100 µM of IKM-159, and then incubated for 1 h at 4° C. Non-specific binding was determined as the amount of radioligand bound in the presence of a saturating concentration of glutamate (1 mM). Total binding was determined as the amount of radioligand bound in the absence of any competing ligands minus the non-specific binding. Experimental variations included a 1 h pre-incubation with IKM-159, an increase in the total binding period to 2 h, and an incubation with a saturating concentration of a known AMPA/KA antagonist, 6-cyano-7-nitroquinoxaline-2,3-dione (10 µM CNQX). Data were presented as a percentage of the total binding. All experimental conditions were performed in duplicate in each assay and then averaged for each trial.

Statistical analysis. At least three separate experiments were performed for each assay. For data involving three or more groups, a one-way analysis of variance (ANOVA) was performed with a Tukey-Kramer post hoc test for comparison amongst the groups. For data involving two groups, an unpaired student's t-test was performed; if the standard deviations between the two groups were statistically significant, a Welsh correction was added. If the data involving three or more groups or data involving two groups where multiple treatments were performed on the same sample, a repeated measures ANOVA and paired t-test were used, respectively, for analysis of significance. Dose-inhibition response curves were fitted, with the maximum value constrained to 100 and the minimum value constrained to values greater than or equal to zero, using the following equation in order to calculate the IC$_{50}$ values:

$$\text{Response} = \text{minimum} + (\text{maximum} - \text{minimum})/(1 + (\text{IC}_{50}^{hill\,slope}/\text{dose}^{hillslope}))$$

All calculations for statistical analysis were carried out with Graphpad Prism4 software (La Jolla, Calif.). Data are presented as mean±S.E.M. with statistical significance set at p<0.05.

Results

IKM compounds reduce excitatory transmission in cultured neurons. Domino metathesis schemes (ring-opening metathesis/cross metathesis/ring-closing metathesis) were used to synthesize a family of "IKM" compounds inspired by the convulsant natural toxins KA and neoDH (FIG. 1) (Ikoma et al., 2008; Oikawa et al., 2009 and unpublished results). The IKM molecules are all heterotricyclic hexahydro-2H-furo[2,3-c]pyrrole-dicarboxylic acids with variable third ring components that include substituted pyrans (IKM-86 and -110), oxepanes (IKM-98 and -107), and tetrahydropyridines (IKM-27 and -159). In mouse behavioral assays, IKM-98, IKM-110 and IKM-107 elicited varying degrees of hyperactivity (Oikawa et al., 2009). In contrast, IKM-27, IKM-86 and IKM-159 induced hypoactive phenotypes similar to cataleptic states (i.e., with marked muscle rigidity, suggesting that their pharmacological activity differed fundamentally from the parent convulsants (Ikoma et al., 2008; Oikawa et al., 2009 and unpublished observations). Here we determined if molecular mechanisms underlying this distinctive behavioral phenotype involved actions on AMPA or kainate receptors.

Figure 2:
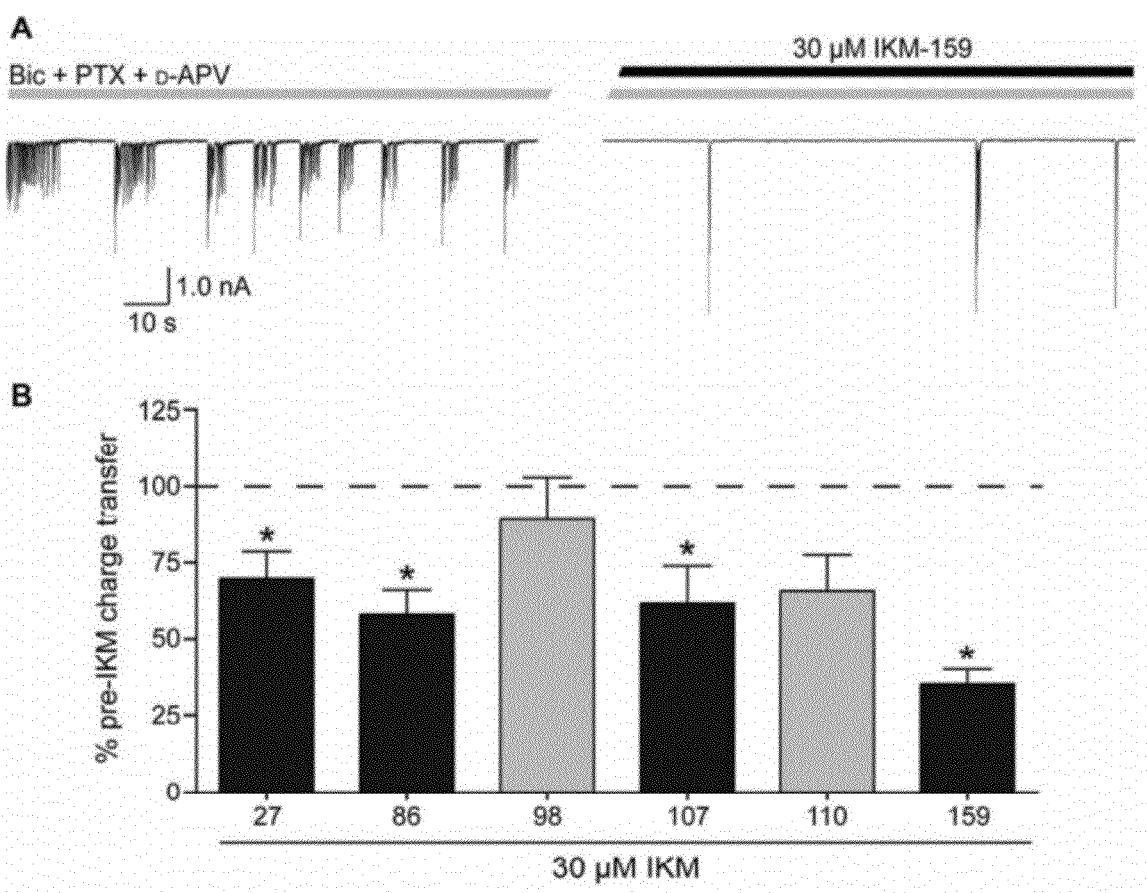
FIG. 2. IKM-159 reduces hippocampal AMPA receptor excitatory drive. A. Representative whole-cell current recording from a primary hippocampal neuron demonstrating a reduction in AMPA receptor-mediated EPSCs during application of 30 μM IKM-159 (right) when compared to the control period (left). B. The effect of IKM molecules was quantified by measuring the charge transfer during bursts of AMPA receptor-mediated synaptic events. The column graph shows reductions in charge transfer in the presence of 30 μM of each IKM compounds as a percent of the charge transfer during the control period (IKM-27, 70±9%; IKM-86, 58±8%; IKM-98, 89±14%; IKM-107, 62±12%; IKM-110, 66±12%; IKM-159; 35±5%, n=3-6 for the compounds tested, p<0.05 for all except IKM-110: p=0.052 and IKM-98, paired t-test). Average initial charge transfer: 6.3±1.0 μA·ms, n=26. Cultured hippocampal neurons were voltage clamped at −70 mV.

We first measured the actions of the IKM compounds on the charge transfer during spontaneously occurring, polysynaptic bursts of AMPA receptor excitatory post-synaptic currents (EPSCs) in cultured hippocampal neurons (recorded in the presence of bicuculline methiodide and picrotoxin to inhibit GABA$_A$ receptors and D-APV to inhibit NMDA receptors). The charge transfer during AMPA EPSCs before IKM application, which had a mean of 6.3±1.0 µA·ms (n=26), was reduced to varying degrees by the compounds. IKM-159 had the greatest inhibitory effect at a fixed concentration of 30 µM, producing a reduction in charge transfer of 65±5% (n=6, p<0.01). The other compounds were less effective, although most showed some degree of inhibitory activity (reduction from control charge transfer: IKM-27, 31±9%; IKM-86, 42±8%; IKM-107, 39±12%; IKM-110, 34±12%, n=3-5, p<0.05 for all except IKM-110: p=0.052, paired t-test) (FIG. 2B). IKM-98 did not significantly impact charge transfer (reduction by 11±14%) but did elicit a robust whole-cell current (380±160 pA, n=3) that was only observed to a lesser extent with IKM-107 (47±11 pA, n=3) (data not shown). Despite the polar chemical nature of the compounds, recoveries to basal EPSC charge transfers were minimal. In summary, these data provided the first indication that AMPA receptors could be a target for IKM activity.

Figure 3:
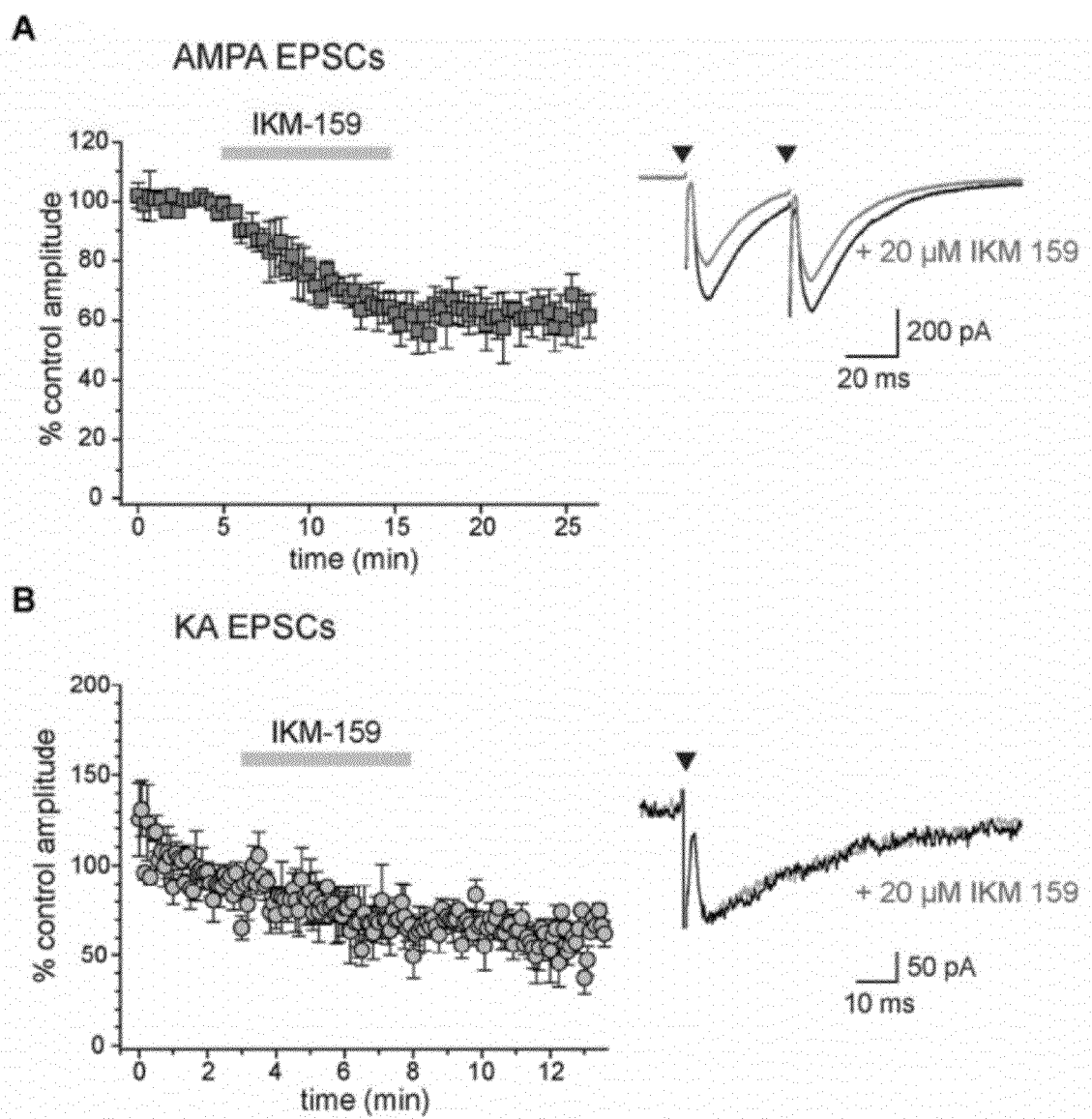
FIG. 3. IKM-159 reduces synaptic AMPA receptor EPSCs amplitudes but does not inhibit kainate receptor EPSCs. A. EPSCs mediated by AMPA receptors were elicited by stimulation of Schaffer collateral inputs to CA1 pyramidal neurons during whole-cell voltage clamp recording from mouse acute brain slices. Left: Summary data of the percent control AMPA EPSC peak amplitudes elicited by Schaffer collateral stimulation during the control period and during application of 20 μM IKM-159 demonstrates a reduction in EPSC peak amplitudes with application of IKM-159 (expressed as a percent of control peak amplitude: IKM-159; 66±5%, n=3, p<0.05, paired t-test). Average control peak AMPA EPSC amplitude: 560±20 pA, n=3. Right: Representative paired-pulse trace from a CA1 pyramidal neuron after stimulation of Schaffer collateral fibers during a control period (black) and during application of 20 μM IKM-159 (gray trace). B. EPSCs mediated by kainate receptors were elicited by stimulation of mossy fiber inputs to CA3 pyramidal neurons during whole-cell voltage clamp recording from mouse acute brain slices. Left: Summary data of the percent control kainate EPSC peak amplitudes. Application of 20 μM IKM-159 did not alter the typical run-down in amplitude observed with these synaptic currents. Average control peak KA EPSC amplitude: 170+40 pA, n=3. Right: Representative single pulse trace from a CA3 pyramidal neuron after stimulation of mossy fibers during a control period (black) and during application of 20 μM IKM-159 (gray trace).

Subsequent pharmacological characterization was focused predominantly on IKM-159 because this compound was the most effective in our initial neuronal recordings. The action of IKM-159 was next tested on AMPA, kainate, and NMDA receptor-mediated EPSCs in a more intact preparation, acute hippocampal slices from mice. As shown in the normalized data in FIG. 3A, IKM-159 (20 µM) reduced the mean amplitude of pharmacologically isolated AMPA receptor EPSCs evoked from Schaffer collateral-CA1 pyramidal cell synapses by 34±5% (control: 560±20 pA; IKM-159, 370±40 pA, n=3, p<0.05). Similar to its effect on bursts of AMPA EPSCs in cultured neurons, the synaptic amplitudes remained depressed for >10 minutes after application of IKM-159. In contrast, IKM-159 did not alter the mean amplitude of mossy fiber-CA3 pyramidal cell kainate receptor-mediated EPSCs, which exhibit a marked time-dependent run-down of approximately 20-40% from initial peak amplitudes (Hirbec et al., 2003; Ito et al., 2004) (FIG. 3B). IKM-159 (20 µM) also did not alter the amplitude of NMDA receptor-mediated EPSCs evoked from Schaffer collateral-CA1 pyramidal cell synapses (99±3% of control amplitudes following a 5 min treatment, n=3, data not shown). Together, these data demonstrate that IKM-159 selectively inhibits AMPA receptors in both acute mouse hippocampal slices and cultured primary hippocampal neurons.

Figure 4:
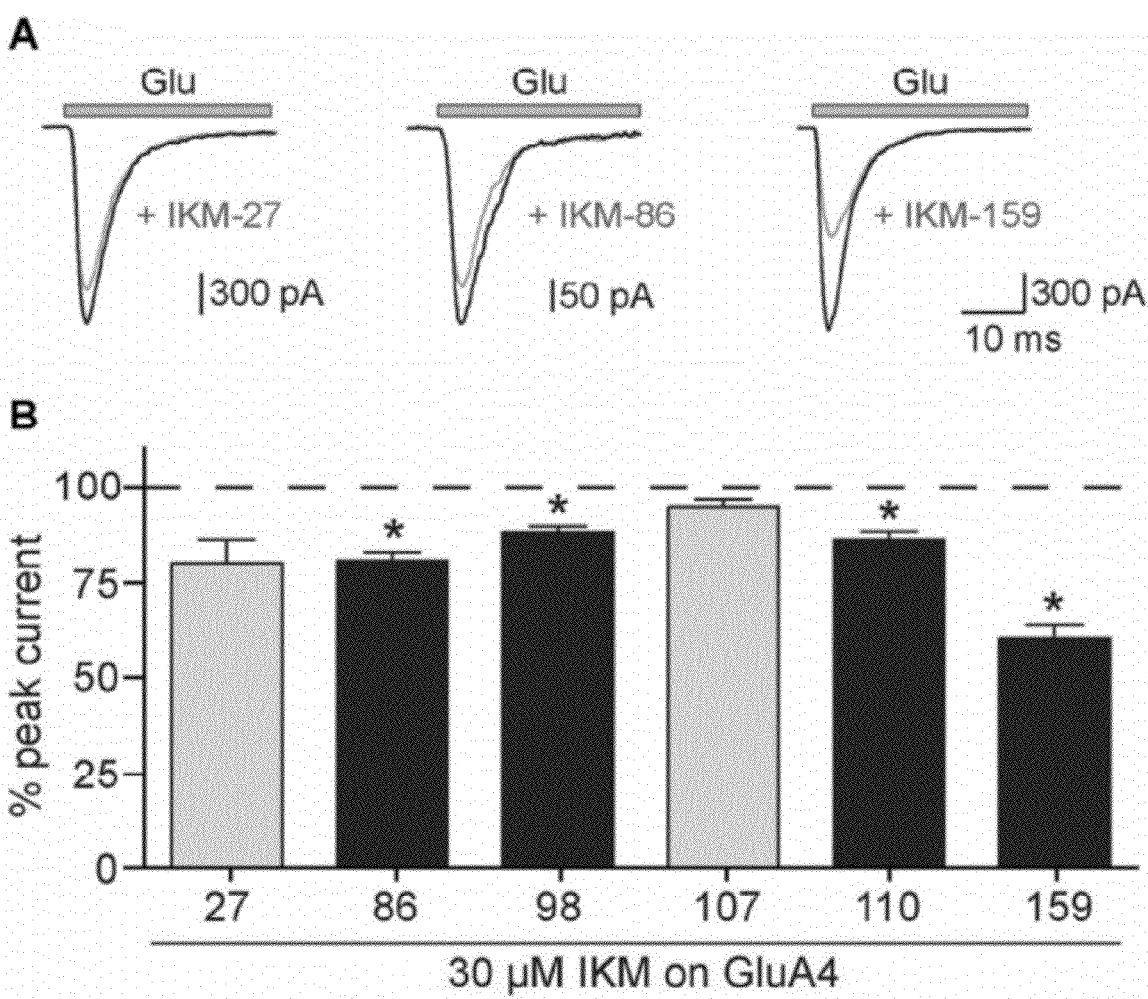
FIG. 4. IKM molecules inhibit GluA4 receptor activation. A. Representative traces from recombinant GluA4 receptors before (black trace) and during (gray trace) co-application of 30 μM IKM-27 (left), 30 μM IKM-86 (middle) and 30 μM IKM-159 (right) with glutamate reveals that IKM-159 inhibits GluA4 currents to a greater degree than IKM-27 or IKM-86. Gray bar denotes a 100 ms application of 10 mM glutamate. All IKM molecules were pre-applied to the receptor-expressing HEK293 cells for at least one minute prior to glutamate application B. The graph shows the percent reduction in peak GluA4 currents in the presence 30 μM of each IKM molecule. IKM-159 inhibits GluA4 peak current amplitudes to the greater degree (expressed as a percent of control amplitude: IKM-27, 80±6%; IKM-86, 81±2%; IKM-98, 88±2%; IKM-107, 95±2%; IKM-110, 86±2%; IKM-159, 60±4, n=3-8 cells for each compound, p<0.05 for IKM-86, -98, -110 and -159, p=0.07 for IKM-27, paired t-test).

IKM-159 may exhibit subunit-selective antagonism of AMPA receptors. We next examined the efficacy of IKM compounds on recombinant AMPA and kainate receptors to determine if the analogs were selective for a particular subset of receptor stoichiometries. As an initial survey of the six IKM compounds, inhibition of recombinant GluA4 receptor activation was measured in whole-cell patch clamp recordings from transfected HEK-293 cells. Currents were elicited rapidly with a 100 ms application of 10 mM glutamate alone and in the presence of the compounds shown in FIG. 1 (30 µM for each IKM analog, pre-applied for at least one minute before glutamate). The IKM compounds inhibited GluA4 receptor peak glutamate currents to differing degrees, with IKM-159 again exhibiting the greatest effect (reduction from control peak amplitudes: IKM-27, 20±6%; IKM-86, 19±2%; IKM-98, 12±2%; IKM-107, 5±2%; IKM-110, 14±2%; IKM-159, 40±4%, n=3-8 cells for each compound, p<0.05 for IKM-86, -98, -110 and -159, p=0.07 for IKM-27, paired t-test). Only the inhibition by IKM-159 was significantly greater relative to the other IKM compounds (p<0.05); conversely, the oxepane analog, IKM -107, was relatively ineffective (FIG. 4A, B).

Figure 5:
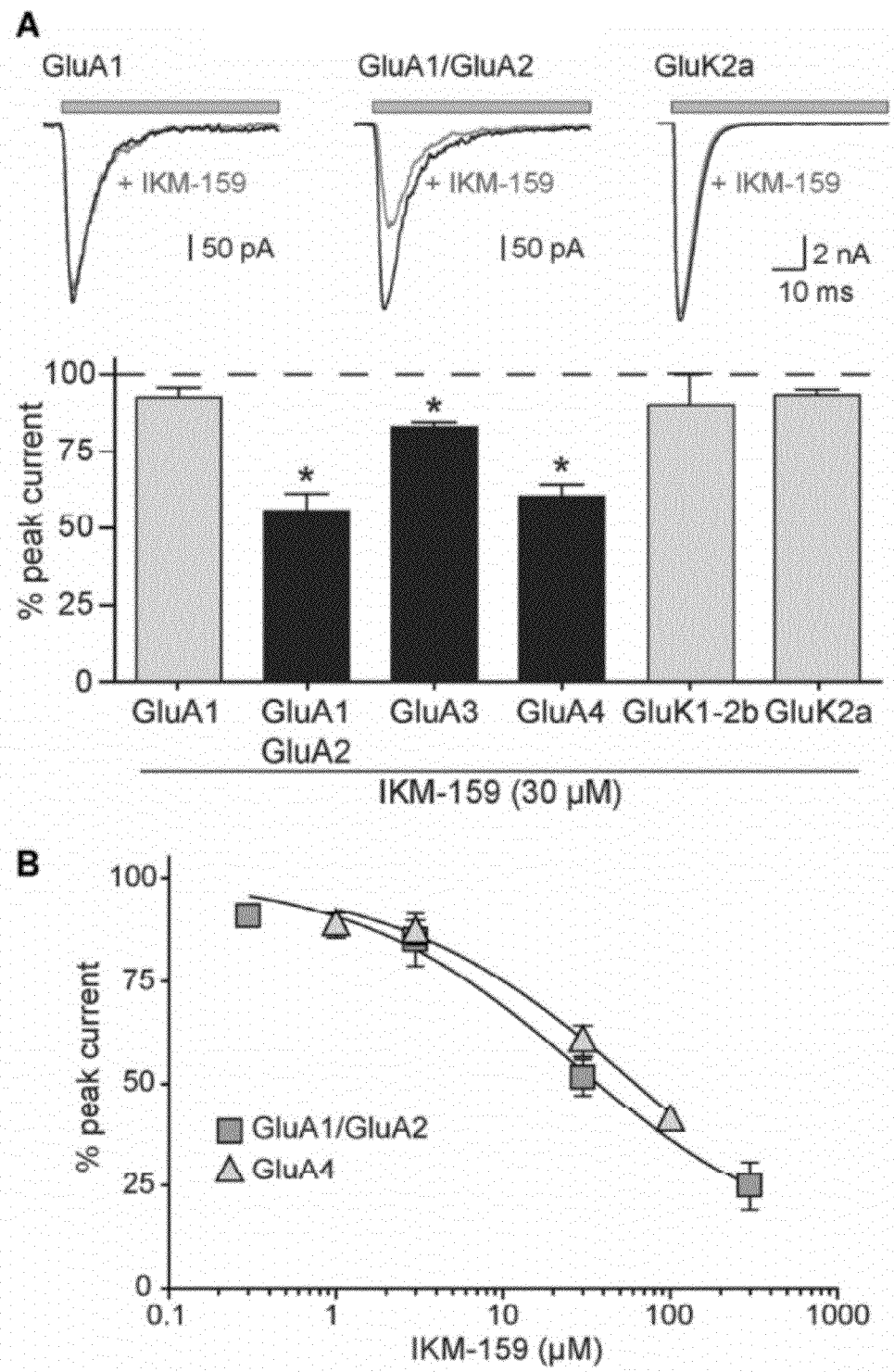
FIG. 5. IKM-159 is more potent on GluA2- and GluA4-containing AMPA receptors. A. Top: Representative traces from AMPA and kainate receptor currents in the absence and presence of IKM-159. Glutamate (100 ms, 10 mM) was applied to recombinant homomeric GluA1 receptors (left), heteromeric GluA1/GluA2 receptors (middle) and homomeric GluK2a receptors (right) in the absence (black trace) and presence (gray trace) of 30 μM IKM-159. IKM-159 was pre-applied to the receptor-expressing HEK293 cells for at least one minute prior to the test glutamate application. Bottom: The graph shows the reduction in mean peak amplitude as a percent of the control current amplitude. At this concentration, IKM-159 inhibits GluA2-containing and GluA4 receptors, modestly inhibits GluA3 receptors, and has no effect on homomeric GluA1, GluK1-2b or GluK2a receptors (expressed as a percent of basal peak amplitude: GluA1, 92±3%; GluA1/GluA2, 56±5%; GluA3, 83±2%; GluA4, 60±4%; GluA1-2b, 90±10%; GluK2a, 93±2%, n=3-8 cells for each receptor, p<0.05 for GluA1/GluA2, GluA3 and GluA4, paired t-test). B. Fitting of concentration-inhibition data with logistic curves yields $IC_{50}$ values of 26±2 μM for GluA1/GluA2 and 60±8 μM for GluA4 receptors. For these curves, the maximum peak current constrained to 100% and the minimum current constrained to values greater than or equal to zero.

AMPA receptors comprised of other subunit combinations were tested next. IKM-159 (30 µM) inhibited heteromeric GluA1/GluA2 receptors and GluA4 homomeric AMPA receptors to roughly an equivalent degree (44±5% and 40±4% reduction in peak current amplitude, n=5 and 8, respectively, p<0.05), had weaker, yet still significant, activity on homomeric GluA3 receptors (17±2% reduction in peak current amplitude, n=4, p<0.05), and did not inhibit activation of homomeric GluA1 receptors (92±3% of glutamate alone peak, n=3, n.s.) (FIG. 5A). Inhibition-response curves were generated for the action of IKM-159 on GluA1/GluA2 and GluA4 AMPA receptors, revealing a slightly higher potency for the heteromeric receptors ($IC_{50}$ values: GluA1/GluA2, 26±2 µM; GluA4 $IC_{50}$, 60±8 µM; currents evoked by 10 mM glutamate) (FIG. 5B). In contrast to its actions on AMPA receptors, IKM-159 did not reduce currents mediated by either homomeric GluK1-2b or GluK2a kainate receptors (90±10% and 93±2% of peak glutamate current, n=3, n.s.) (FIG. 5A). Thus, these results demonstrate that IKM-159 acts as an AMPA receptor-selective antagonist with preference for GluA1/GluA2 at the concentrations tested in these studies.

Figure 6:
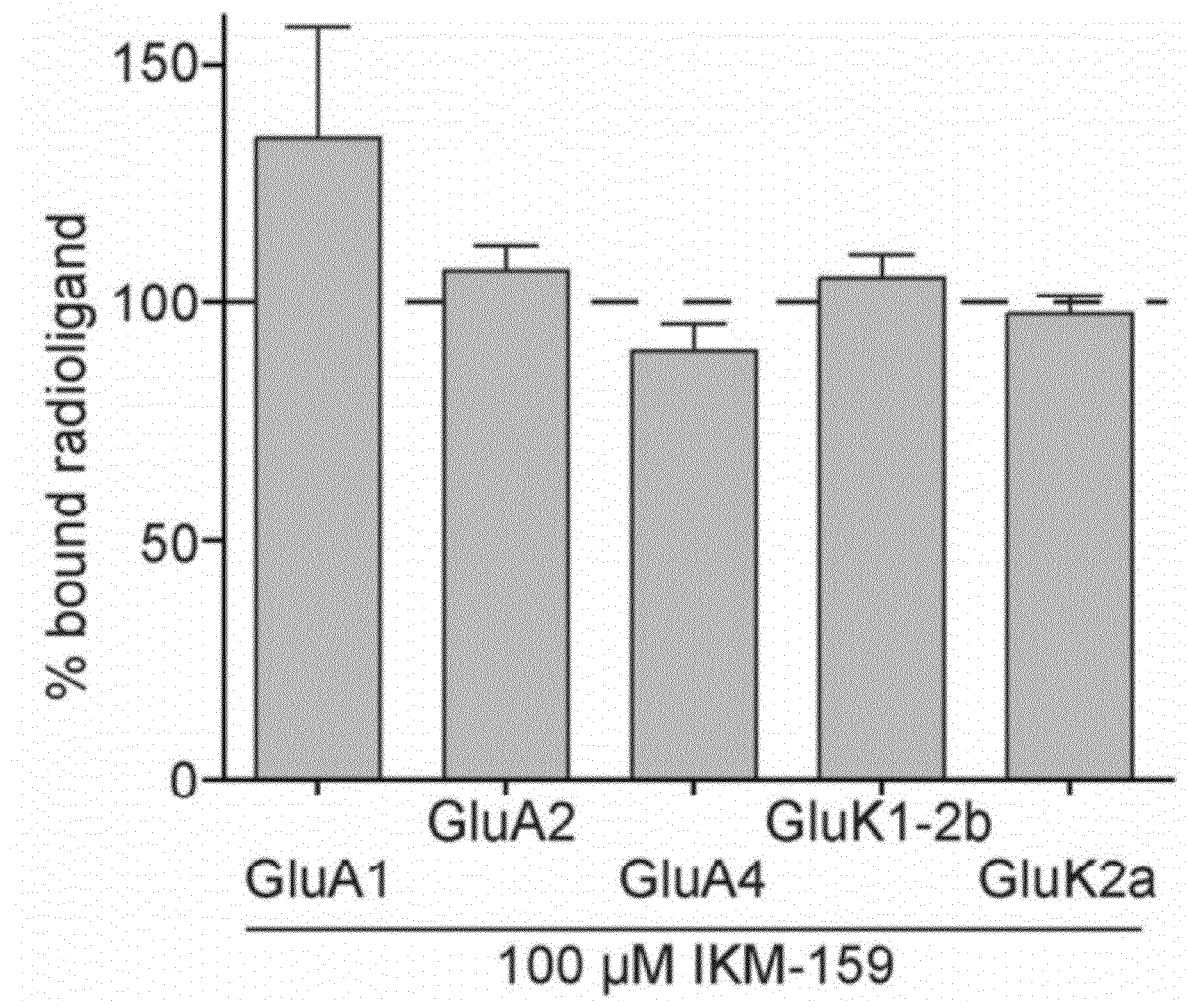
FIG. 6. IKM-159 does not displace radiolabeled ligand from AMPA or kainate receptors. IKM-159 (100 μM) competed with either [$^3$H]AMPA or [$^3$H]KA for binding to membranes prepared from HEK293-T/17 cells expressing AMPA or kainate receptor subunits, respectively. No displacement was observed for any receptors (expressed as a percent of the total binding in the absence of competing ligands: GluA1, 134±23%; GluA2, 107±5%; GluA4, 90±6%; GluK1-2b, 105±5%; GluK2a, 98±4%, n=3-4 trials for each receptor).

IKM-159 inhibition: competitive or non-competitive? The IKM molecules failed to displace radioligand from iGluR proteins in rat brain membranes in earlier studies (Ikoma et al., 2008; Oikawa et al., 2009), leading to the conclusion that they did not directly interact with AMPA, kainate, or NMDA receptors. Given that our physiological studies clearly supported antagonist activity on AMPA receptors, we further explored the nature of this activity in additional radioligand binding assays with recombinant receptor subunits expressed in HEK-293 cells. Consistent with the earlier results, a physiologically active concentration of IKM-159 (100 µM) failed to displace either [$^3$H]-AMPA from GluA1, GluA2, or GluA4 receptors or [$^3$H]-KA from recombinant GluK1 or GluK2 KA receptors (expressed as percent of specific binding in absence of IKM-159: GluA1, 135±23%; GluA2, 107±5%; GluA4, 90±6%; GluK1-2b, 105±5%; and GluK2a, 98±4%, n=3-4 trials for each cDNA construct) (FIG. 6). As a positive control for the displacement assay conditions, we confirmed in parallel experiments that 10 µM 6-cyano-7-nitroquinoxaline-2, 3-dione (CNQX), a competitive antagonist for AMPA and kainate receptors, effectively competed for GluA2 receptor binding (82% displacement of the radioligand; data not shown). Two alternate reaction conditions also were tested to determine if the absence of displacement occurred because binding of IKM-159 failed to reach equilibrium during the incubation with membrane preparations. We measured the percent of [$^3$H]-AMPA bound after (i) a 1 h pre-incubation with 100 µM IKM-159 prior to addition of the radioligand, and (ii) a 2 h incubation of 100 µM IKM-159 with [$^3$H]-AMPA. Neither condition resulted in any significant displacement of [$^3$H]-AMPA from GluA4 homomeric receptors (100% and 113% bound radioligand, respectively, data not shown). At face value, these results suggest that IKM-159 acts as a non-competitive antagonist of AMPA receptors.

Figure 7:
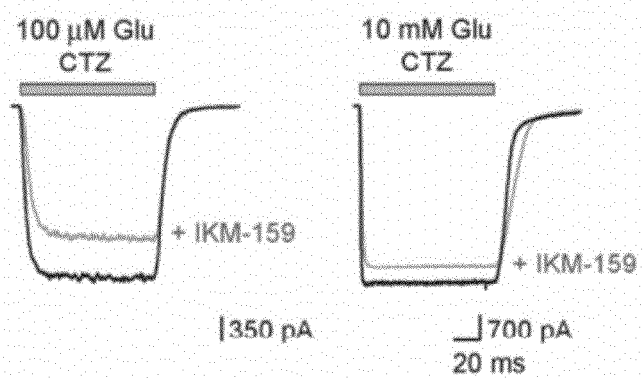
FIG. 7. Inhibition of GluA4 receptors by IKM-159 is dependent upon the agonist concentration. A. Representative steady-state currents evoked from GluA4 AMPA receptors by two concentrations of glutamate (100 μM and 10 mM) in the presence of cyclothiazide (100 μM). Black traces were recorded before co-application of the antagonist, whereas gray traces were evoked in the presence of IKM-159 (30 μM). The graph shows that IKM-159 inhibited currents evoked by the lower concentration to a greater degree. B. A similar experiment in which the agonist KA was used at two different concentrations (50 and 500 μM). The graph shows that currents evoked by 50 μM KA were inhibited to a greater degree by IKM-159. C. In contrast to the preceding experiments, IKM-159 inhibition of peak glutamate-evoked currents did not vary with agonist concentration (in this case, 500 μM and 10 mM). The antagonist IKM-159 was pre-applied to the receptor-expressing HEK293-T/17 cells for at least one minute prior to the test agonist in the experiments shown in A-C.
Figure 7:
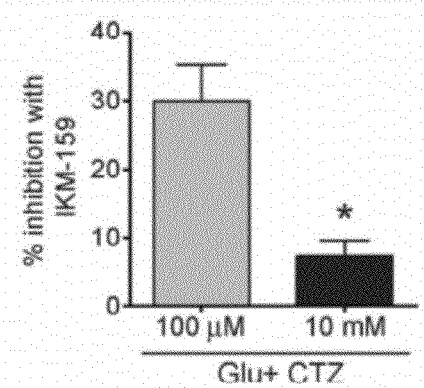
Figure 7:
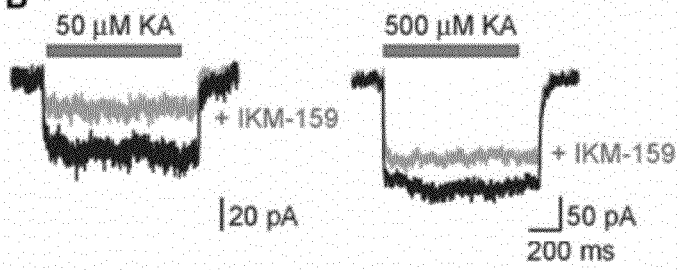
Figure 7:
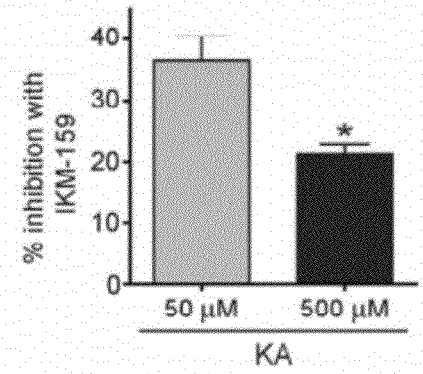
Figure 7:
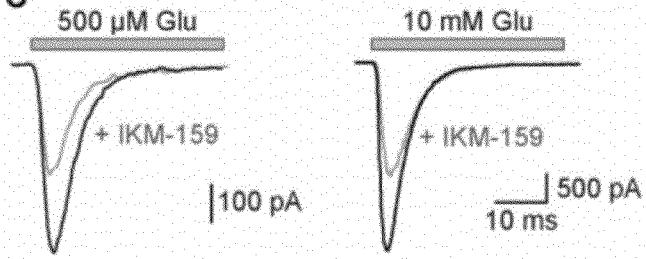
Figure 7:
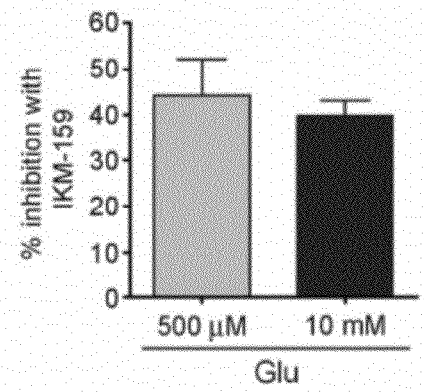

These results of the binding assays were surprising, however, because it seemed rather improbable that AMPA receptor antagonists containing cyclized glutamate backbones (albeit with distinct stereochemistry) would interact serendipitously with an allosteric domain removed from the receptor ligand-binding site. For that reason, we carried out additional physiological experiments designed to test the mechanistic nature of IKM-159 antagonism. We tested if the magnitude of IKM-159 inhibition of GluA4 receptor activation varied dependent upon agonist concentration, which would be consistent with a competitive mechanism of action. Steady-state GluA4 receptors currents were elicited with two concentrations of glutamate (100 µM and 10 mM) in the presence of 100 µM cyclothiazide (CTZ), which prevented desensitization of these receptors (Fletcher et al., 1996; Wong et al., 1993). We found that 30 µM IKM-159 reduced steady-state currents elicited by 100 µM glutamate to a greater degree than those with 10 mM glutamate (percent inhibition: 30±5% versus 7±2%, respectively n=4; p<0.05) (FIG. 7A). We confirmed the agonist concentration-dependence of inhibition in an additional experiment with kainate, a partial agonist that predominantly activates a small equilibrium current from GluA4 and other AMPA receptors (Patneau et al., 1993; Stern-Bach et al., 1998). Similar to the findings from glutamate application, 30 µM IKM-159 inhibited kainate-evoked steady state currents to greater degree at a lower (50 µM KA) agonist concentration than at a higher (500 µM KA) agonist concentration (percent inhibition: 37±4%, n=4 versus 21±2%, respectively, n=5; p<0.05) (FIG. 7B). However, when we measured the inhibition of GluA4 non-equilibrium peak currents elicited by application of 500 µM and 10 mM glutamate, we observed no significant difference in inhibition with application of 30 µM IKM-159 (percent inhibition: 44±8%, n=5 versus 40±3%, respectively, n=9; n.s.) (FIG. 7C). In summary, reduction of steady-state currents by IKM- 159 was agonist concentration-dependent, in contrast to inhibition of peak, non-desensitized currents. Taken together, the results of the electrophysiology and binding studies support a complex mechanism of action for IKM-159 that is inconsistent with either simple competitive or state-independent allosteric inhibition.

Figure 8:
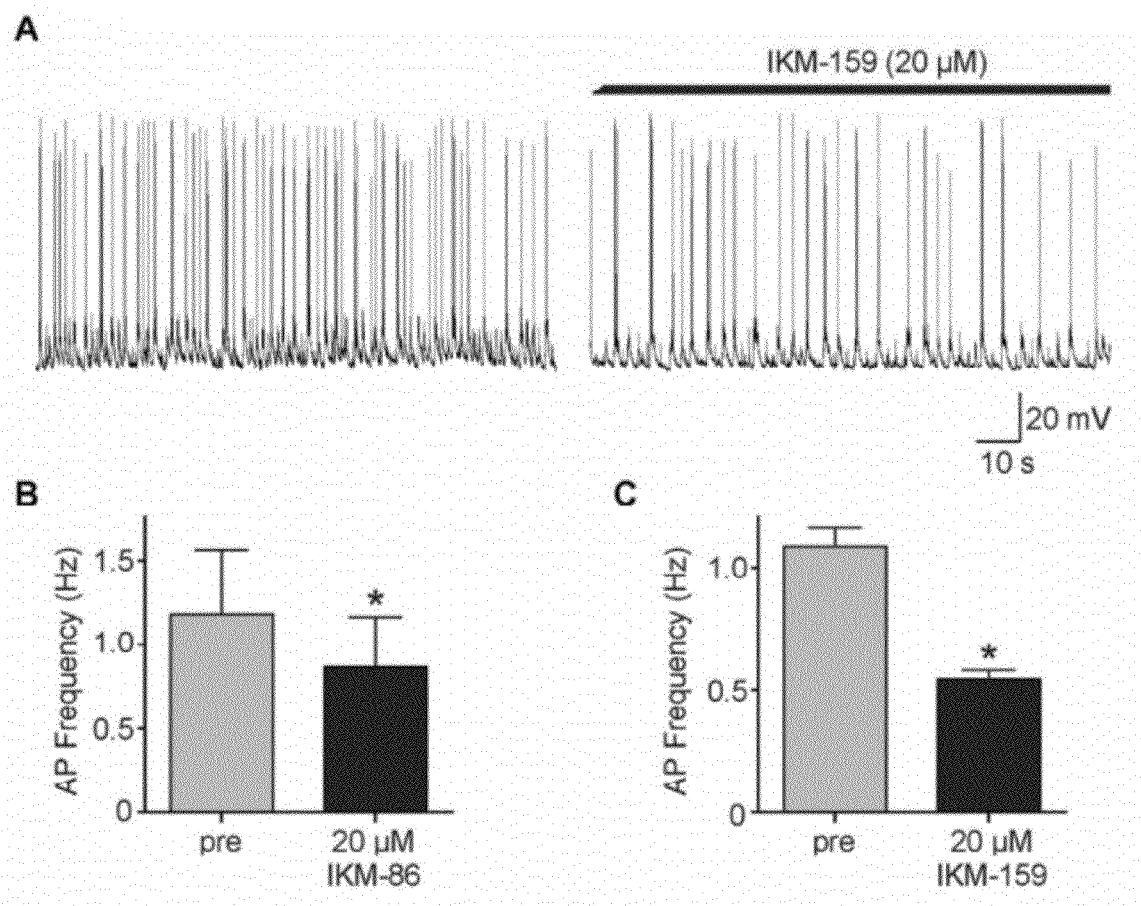
FIG. 8. IKM-159 reduces basal neuronal excitability. A. Representative current clamp recording from a primary hippocampal neuron in the absence and presence of 20 μM IKM-159 illustrating the reduction in basal action potential (AP) firing frequency. B, C. AP frequencies during the control period and in the presence of 20 μM IKM-86 (B) and 20 μM IKM-159 (C). the basal firing frequency is significantly reduced by the antagonists (B. pre, 1.2±0.4 Hz versus IKM-86, 0.9±0.3 Hz, n=6, p<0.05, paired t-test) (C. pre, 1.1±0.07 Hz versus IKM-159, 0.5±0.04 Hz, n=3, p<0.05, paired t-test).

Effects of IKM-159 on neuronal excitability. The behavioral response to IKM-159 and IKM-86 is one of marked hypoactivity and immobility, which differs from behaviors associated with non-selective AMPA receptor antagonists, such as CNQX, and NMDA antagonists such as MK-801 and memantine (Czlonkowska et al., 1997; Fredriksson et al., 2002; Ikoma et al., 2008; Maj et al., 1995). To determine if altered neuronal excitability could contribute to this behavioral phenotype, we examined the effect of IKM-86 and IKM-159 on action potential firing in cultured hippocampal neurons. Spontaneous action potentials were recorded in current-clamp mode before, during and after application of 20 µM IKM-86 and IKM-159. The firing frequency was reduced modestly from 1.2, 0.4 Hz to 0.9, 0.3 Hz by IKM-86 (n=6, $p<0.05$; FIG. 8B) and to a greater degree, from 1.1, 0.1 Hz to 0.5, 0.04 Hz by IKM-159 (n=3, $p<0.05$, FIG. 8A, C). Similar to the effect of IKM compounds on neuronal AMPA EPSC charge transfer, this reduction in action potential firing frequency was prolonged after removal of IKM-86 and IKM-159.

Figure 9:
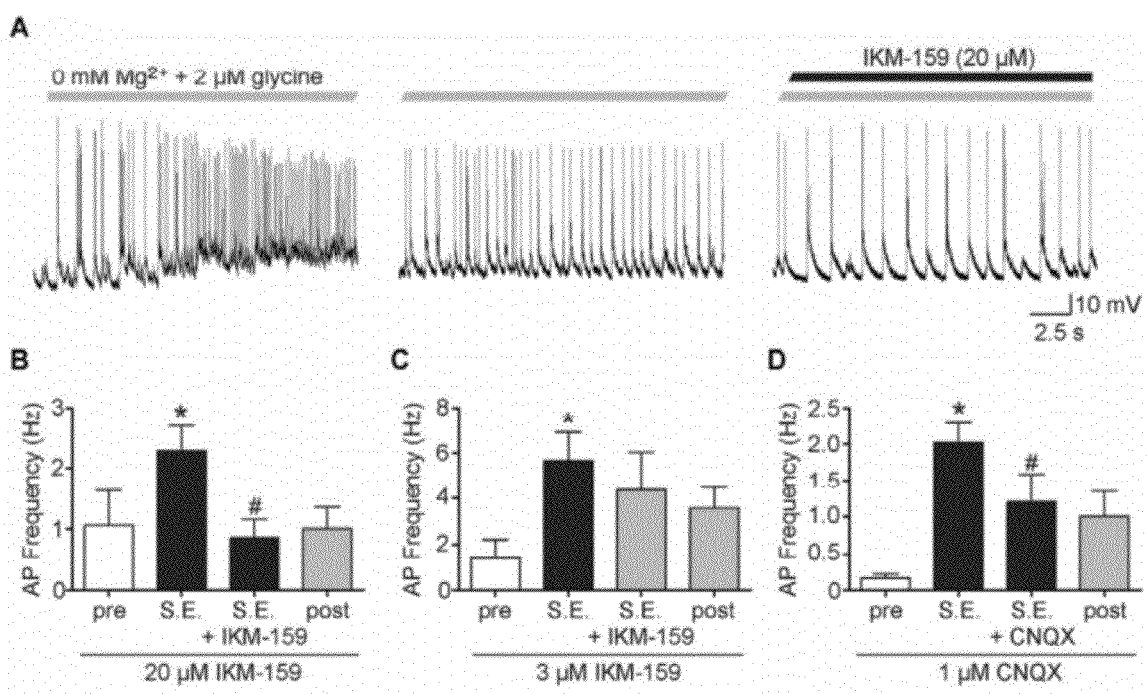
FIG. 9. IKM-159 reduces neuronal hyperexcitability in an in vitro model of status epilepticus (SE). A. Representative current clamp recording from a primary hippocampal neuron upon induction of SE (by removal of $Mg^{2+}$ and addition of 2 μM glycine), following stabilization of high-frequency AP firing, and in the presence of IKM-159 (20 μM). B-D. AP frequencies before SE induction, during a stable SE state (>2 Hz), in the presence of IKM-159 or CNQX, and 10 minutes after removal of the compound. IKM-159 was tested at concentrations of 20 μM (B) and 3 μM (C), whereas CNQX was used at 1 μM (D). Mean AP frequencies in each condition are given in the text. All data were analyzed using a repeated measures ANOVA with Tukey-Kramer post hoc test. * denotes statistical significance when compared to control AP frequency while # denotes statistical significance when compared to SE AP frequency.

Several AMPA receptor selective antagonists reduce neuronal hyperactivity in both acute brain slice preparations and in in vitro models of epilepsy (Grasso et al., 1999; Szabados et al., 2001). Non-competitive AMPA receptor antagonists also have demonstrated therapeutic potential for epilepsy in interim analysis of pre-clinical trials (Bialer et al., 2002; Howes et al., 2007). We therefore tested the efficacy of IKM-159 in reducing the hyperactive neuronal phenotype in dissociated hippocampal neurons using an in vitro model of status epilepticus (SE) (Deshpande et al., 2007; Pal et al., 1999). Action potential firing frequencies were elevated and membrane potentials depolarized following removal of extracellular magnesium from the external bath and concomitant application of 2 µM glycine (FIG. 9A, top left). A period of depolarization-induced channel inactivation ensued, followed by a slow hyperpolarization and a return of action potential firing to an average frequency of >2 Hz (Deshpande et al., 2007; Pal et al., 1999) (FIG. 9A, top center). Addition of IKM-159 (20 µM) to the bath significantly reduced the hyperactive firing frequencies to near basal levels (SE condition, 2.3±0.4 Hz; with IKM-159, 0.9±0.3 Hz, n=3, $p<0.05$) (FIG. 9A top right, 9B). We observed no return in AP firing frequency to hyperactive frequencies upon wash out of IKM-159 (1.0±0.3 Hz; FIG. 9B). A lower concentration of IKM-159 (3 µM) was less effective (SE condition, 5.7±1.2 Hz; with IKM-159, 4.3±1.7 Hz, n=3; n.s., FIG. 9C), suggesting that the reduction in neuronal excitability could be accounted for predominantly by AMPA receptor inhibition. Thus, IKM-159 effectively reduces the seizure-like phenotype in an in vitro SE model, in a concentration range similar to that which inhibited AMPA receptors. In parallel experiments with the SE model, the non-selective AMPA and kainate receptor antagonist CNQX (1 µM) similarly reduced AP firing frequency (SE, 2.0±0.3 Hz; with CNQX, 1.2±0.4, n=4, $p<0.05$) (FIG. 9D). These results are consistent with AMPA receptor inhibition as the principle pharmacological activity of IKM-159 that underlies its effects on neuronal excitability, although they do not preclude contributions by other receptor signaling systems to the behavioral phenotype.

Discussion

Aberrant iGluR signaling is central to a variety of neurological diseases (e.g., epilepsy, stroke, and pain) (Ben-Ari, 2001; Jensen, 2002), and therefore antagonists with subunit selectivity could be of substantive pharmacological and clinical utility. The unusual behavioral activity observed previously with some of the IKM compounds led us to examine their pharmacological activities in detail. Several intriguing points emerged from this analysis. Most notably, we found that the tetrahydropyridine analog IKM-159 acts as the first AMPA receptor-selective antagonist that demonstrates partial subunit specificity for GluA2-, GluA3- and GluA4-containing receptors. Furthermore, application of IKM-159 reduced neuronal hyperexcitability in an in vitro model of status epilepticus, most likely through inhibition of AMPA receptors. In addition to the novel pharmacological profile, the potential utility of this and related compounds resides in the high-efficiency, relatively simple synthetic pathways that have been established previously (Ikoma et al., 2008; Oikawa et al., 2009). We therefore propose that IKM-159 could serve as a structural template for a series of more potent AMPA receptor-selective antagonists possessing greater therapeutic potential.

Pharmacological activity of IKM-159. While their synthesis was inspired by the high-affinity kainate receptor agonists KA and neoDH, the structure of IKM-159 and other analogs differs substantially from the parent convulsant, and it was therefore possible that their mechanism of action diverged from actions on iGluRs (particularly in the case of those that induced hypoactivity). Indeed, we found that synaptic kainate receptors at mossy fiber synapses, which are a heteromeric combination of the GluK2, GluK4, and GluK5 subunits (Contractor et al., 2003; Fernandes et al., 2009; Mulle et al., 1998), were unaffected by the compound. IKM-159 instead acts directly on AMPA receptors in neuronal and recombinant systems to reduce channel activation, and, indeed, has a substantially altered pharmacological profile relative to KA and neoDH. In acute hippocampal slices, application of IKM-159 inhibited Schaffer-collateral CA1 EPSCs, which is thought to be predominantly composed of heteromeric GluA1/GluA2 or GluA2/GluA3 AMPA receptors (Lu et al., 2009; Malinow et al., 2002). The degree of CA1 EPSC inhibition was generally consistent with what was observed with GluA1/GluA2 receptors in heterologous systems.

It will be of interest to determine if this apparent subunit selectivity extends to differential activity at a variety of excitatory synapses. If so, IKM-159 could prove to be a valuable pharmacological tool for dissecting fundamental contributions to excitatory transmission by receptors of different subunit composition, which is not possible with the current collection of AMPA receptor antagonists. To date, few AMPA receptor-selective antagonists are commercially available, with GYKI 52466 and the related, more potent non-competitive antagonist, GYKI 53655, as often-employed compounds (Bleakman et al., 1996; Wilding et al., 1995). Both GYKI compounds inhibit AMPA receptors in the low micromolar range, but neither demonstrates any significant selectivity between AMPA receptor subunits (Bleakman et al., 1996). Evans Blue dye (EB) is one of the few AMPA receptor antagonists that exhibits subunit selectivity. Like GYKI 53655, EB is a non-competitive AMPA receptor antagonist with an $IC_{50}$ in the high nanomolar-low micromolar range, but, unlike GYKI 53655, EB selectively inhibits recombinant homomeric GluA1, GluA2 and GluA4 and heteromeric GluA1/GluA2 AMPA receptors (Keller et al., 1993; Weigand et al., 1998). Further analysis of IKM-159 activity at higher concentrations was precluded in the current studies by limitations in the availability of the compound, but additional syntheses in the future will provide rigorous and quantitative comparison of the pharmacological selectivity and determination of the maximal efficacy of the antagonist on GluA 1/GluA2, GluA3 and GluA4 receptors. As well, we will determine how other IKM compounds might overlap in their pharmacological activity and subunit selectivity. Clearly IKM-127, IKM-86 and IKM-159 share overlapping actions on AMPA receptors, while other IKM molecules (-98 and -107) elicit whole cell currents from hippocampal neurons but not in recombinant systems, which suggests activity on unknown population of channels or receptors in addition to their weak activity on AMPA receptors.

Mechanism of antagonism of IKM-159. Determining the mechanism of IKM-159 antagonism proved more complex than first anticipated. Competitive AMPA receptor antagonists such as CNQX readily displace radio-labeled ligands from binding sites on AMPA receptors (e.g., Dev et al., 1996), but a high concentration of IKM-159 did not displace [$^3$H]-AMPA from any recombinant non-NMDA receptors. This data, in combination with earlier results noting an absence of radioligand displacement by IKM molecules from rat brain membranes (Ikoma et al., 2008; Oikawa et al., 2009), suggested that compounds act as a non-competitive antagonists. However, in our current studies we observed that the degree of inhibition of steady-state currents elicited by application of IKM-159 was dependent on agonist concentration. It remains unclear to us why results from the displacement assays and the physiological measures do not correlate; this dichotomy was not observed previously in similar analyses of natural or synthetic analogs of neoDH (Lash et al., 2008; Sanders et al., 2005). It is possible that IKM-159 inhibits AMPA receptors in a state-dependent manner, and that the conformational state present in equilibrium conditions during displacement assays is not the functionally relevant state accessed by IKM-159, resulting in an absence of detectable binding affinity. State dependence of the antagonist activity is consistent with our analysis of the inhibition of steady-state and peak currents by IKM-159; we observed a significantly greater degree of inhibition for peak glutamate currents (40%) when compared to inhibition of steady-state currents evoked by the partial agonist, kainate (21%), or glutamate in the presence of cyclothiazide (7%). Indeed, the latter set of data demonstrated that the antagonist was largely ineffective if the receptors were activated with saturating glutamate concentrations while desensitization was eliminated with cyclothiazide. Resolution of these questions regarding the mechanism of action of IKM-159 will be pursued using more rigorous pharmacological analyses, including a Schild analysis, which will be possible following additional synthetic efforts. Despite the lack of a clearly elucidated mechanism of antagonism, these data underscore the importance of carrying out multiple functional tests in addition to radioligand binding assays when assessing the competitive or non-competitive nature of an antagonist.

Structural contributions to IKM activity. The similarity in structure of the IKM molecules studied here, and their varying pharmacological activities, allow us to draw some limited conclusions regarding the importance of defined chemical elements to their biological properties. For example, molecules that differed in the substitution of a pyran oxygen (IKM-110) for a tetrahydropyridine nitrogen (IKM-27) in the variable third ring largely overlap in their inhibitory action on neuronal and recombinant AMPA receptors. Substitution of the hydroxyl groups on the pyran ring (IKM-86 vs. IKM-110) clearly increased both in vivo and in vitro AMPA receptor antagonist activity, although these functional groups clearly do not appear to play the critically important role in receptor selectivity and affinity observed for the analogous moieties in neoDH (Sanders et al., 2005). Addition of a carbonyl oxygen within the pyrrolidine ring (IKM-27 vs. IKM-159) significantly increased inhibition of both recombinant GluA4 glutamate-evoked currents and in vitro neuronal AMPA receptor EPSC charge transfer, suggesting that this functional group plays an important role in determining potency of the antagonism. Finally, modification of the ring size produced heterogeneous effects on AMPA receptor inhibition by the IKM compounds. Increasing the size of the third ring, from a six-membered pyran ring to a seven-membered oxepane ring, had minimal effect when comparing the actions of IKM-110 and IKM-98 on recombinant glutamate-evoked GluA4 currents but clearly was unfavorable in the case of IKM-107, which was less potent than IKM-86. As well, both oxepanes, IKM-98 and IKM-107, elicited a whole cell current in the presence of $GABA_A$, and NMDA receptor antagonists, which could underlie the hyperactivity elicited by injection of these two IKM compounds in mice (Ikoma et al., 2008). This activity is unlikely to be mediated by AMPA receptors, because IKM-98 had no effect on recombinant AMPA receptors and a very modest impact on charge transfer during bursts of AMPA receptor EPSCs in neurons. The data therefore suggests that enlarging the third ring size promotes associated with a new, uncharacterized target that depolarizes neurons and thereby promotes hyperactivity. In conclusion, the two molecular constituents critical for AMPA receptor antagonism within this group of molecules are the tetrahydropyridine third ring and the presence of an oxo group in the first pyrrolidine ring.

AMPA receptor antagonism as a therapeutic strategy. Over-activation of iGluRs and inflammatory signaling has been implicated in several CNS excitotoxic diseases (Ben-Ari, 2001; Jensen, 2002). iGluR inhibition effectively alleviates detrimental outcomes in both in vivo and in vitro disease models (Gigler et al., 2007; Namba et al., 1994; O'Neill et al., 1998; Smith et al., 2000), However, the therapeutic promise of non-selective iGluR antagonists has fallen short in therapeutic efficacy in clinical trials (Hoyte et al., 2004; Wood, 2005). This failure, in part, could result from inhibition of iGluRs involved in physiological signaling by very potent, non-selective iGluR antagonists. Therefore, therapeutic strategies based on iGluR antagonists with a higher degree of selectivity may prove more successful by sparing excitatory transmission while reducing excitotoxicity.

The pursuit of iGluR subunit-selective agents has been most successful for the NMDA receptor, particularly for the GluN2B subunit [e.g. ifenprodil, traxoprodil (CP 101166) and Ro 25-6981] with the GluN2B subunit-selective NMDA receptor antagonist, CP 101606, recently demonstrating efficacy in modestly reducing dyskinesia and Parkinsonism (Gogas, 2006; Nutt et al., 2008). As discussed earlier, however, analogous highly subunit-selective antagonists for AMPA receptors remain to be developed. AMPA receptors have shown efficacy in a range of animal CNS injury models, and early interim results from pre-clinical trials support the targeting of AMPA receptors for reducing the number and severity of epileptic episodes (Howes et al., 2007). In this current study, we observed that IKM-159, an AMPA receptor-selective antagonist, significantly reduced increased neuronal AP firing frequency in an in vitro model of status epilepticus to near basal AP firing frequency suggesting that this compound could serve as a useful starting point for the development of potentially clinically relevant subunit-selective antagonists. Furthermore, selective AMPA receptor antagonism could be employed not only for epilepsy, but also for the treatment of viral encephalomyelitis (Greene et al., 2008), cerebral ischemia (Gigler et al., 2007), and glioblastomas (Grossman et al., 2009), which have all been ameliorated with application of the AMPA receptor antagonist talampanel.

Here, we have detailed the pharmacological profile of novel series of heterotricyclic glutamate analogues, whose generation was inspired by diversity-oriented synthesis techniques designed to increase structural diversity. IKM-159, the most potent of this first generation of IKM compounds, acts as an AMPA receptor-selective antagonist with no inhibitory action on kainate receptors. These molecules could prove to be useful tools for the mechanistic dissection of AMPA receptor diversity and could serve as structural templates for the design of second generation, higher-potency antagonists.

REFERENCES

Alexander S P, Mathie A, Peters J A (2008). Guide to Receptors and Channels (GRAC), 3rd edition. *Br J Pharmacol* 153: S1-209.

Ben-Ari Y (2001). Cell death and synaptic reorganizations produced by seizures. *Epilepsia* 42 Suppl 3: 5-7_Bialer M, Johannessen S I, Kupferberg H J, Levy R H, Loiseau P. Perucca E (2002). Progress report on new antiepileptic drugs: a summary of the Sixth Eilat Conference (EILAT VI). *Epilepsy Res* 51: 31-71.

Bleakman D, Ballyk B A, Schoepp D D, Palmer A J, Bath C P, Sharpe E F, et al. (1996). Activity of 2,3-benzodiazepines at native rat and recombinant human glutamate receptors in vitro: stereospecificity and selectivity profiles. *Neuropharmacology* 35: 1689-1702.

Contractor A, Sailer A W, Darstein M, Maron C, Xu J, Swanson G T, et al. (2003). Loss of kainate receptor-mediated heterosynaptic facilitation of mossy-fiber synapses in KA2$^{-/-}$ mice. *J Neurosci* 23: 422-429.

Cordier C, Morton D, Murrison S, Nelson A, O'Leary-Steele C (2008). Natural products as an inspiration in the diversity-oriented synthesis of bioactive compound libraries. *Nat Prod Rep* 25: 719-737.

Czlonkowska A, Siemiatkowski M, Plaznik A (1997). Some behavioral effects of AMPA/kainate receptor agonist and antagonists. *J Physiol Pharmacol* 48: 479-488.

Deshpande L S, Lou J K, Mian A, Blair R E, Sombati S, DeLorenzo R J (2007). In vitro status epilepticus but not spontaneous recurrent seizures cause cell death in cultured hippocampal neurons. *Epilepsy Res* 75: 171-179.

Dev K K, Petersen V, Honore T, Henley J M (1996). Pharmacology and regional distribution of the binding of 6-[3H]nitro-7-sulphamoylbenzo[f]-quinoxaline-2,3-dione to rat brain. *J Neurochem* 67: 2609-2612.

Fernandes H B, Catches J S, Petralia R S, Copits B A, Xu J, Russell T A, et al. (2009). High affinity subunits are necessary for ionotropic, but not metabotropic signaling by neuronal kainate receptors. In review.

Fletcher E J, Lodge D (1996). New developments in the molecular pharmacology of alpha-amino-3-hydroxy-5-methyl-4-isoxazole propionate and kainate receptors. *Pharmacol Ther* 70: 65-89.

Fredriksson A, Archer T (2002). Functional alteration by NMDA antagonist: effects of L-Dopa, neuroleptics drug and postnatal administration. *Amino acids* 23: 111-132.

Gigler G, Moricz K, Agoston M, Simo A, Albert M, Benedek A, et al. (2007). Neuroprotective and anticonvulsant effects of EGIS-8332, a non-competitive AMPA receptor antagonist, in a range of animal models. *Br J Pharmacol* 152: 151-160.

Gogas K R (2006). Glutamate-based therapeutic approaches: NR2B receptor antagonists. *Curr Opin Pharmacol* 6: 68-74.

Grasso S, De Sarro G, De Sarro A, Micale N, Zappala M, Puia G, et al. (1999). Synthesis and anticonvulsant activity of novel and potent 2,3-benzodiazepine AMPA/kainate receptor antagonists. *J Med Chem* 42: 4414-4421.

Greene I P, Lee E Y, Prow N, Ngwang B, Griffin D E (2008). Protection from fatal viral encephalomyelitis: AMPA receptor antagonists have a direct effect on the inflammatory response to infection. *Proc Natl Acad Sci USA* 105: 3575-3580.

Grossman S A, Ye X, Chamberlain M, Mikkelsen T, Batchelor T, Desideri S, et al. (2009). Talampanel with standard radiation and temozolomide in patients with newly diagnosed glioblastoma: a multicenter phase II trial. *J Clin Oncol* 27: 4155-4161.

Hirbec H, Francis J C, Lauri S E, Braithwaite S P, Coussen F, Mulle C, et al. (2003). Rapid and differential regulation of AMPA and kainate receptors at hippocampal mossy fibre synapses by PICK1 and GRIP. *Neuron* 37: 625-638.

Hollmann M, Heinemann S (1994). Cloned glutamate receptors. *Annu Rev Neurosci* 17: 31-108.

Howes J F, Bell C (2007). Talampanel. *Neurotherapeutics* 4: 126-129.

Hoyte L, Barber P A, Buchan A M, Hill M D (2004). The rise and fall of NMDA antagonists for ischemic stroke. *Curr Mol Med* 4: 131-136.

Ikoma M, Oikawa M, Gill M B, Swanson G T, Sakai R, Shimamoto K. et al. (2008). Regioselective Domino Metathesis of 7-Oxanorbornenes and Its Application to the Synthesis of Biologically Active Glutamate Analogues. *European J Org Chem* 2008: 5215-5220.

Ito K, Contractor A, Swanson G T (2004). Attenuated plasticity of postsynaptic kainate receptors in hippocampal CA3 pyramidal neurons. *J Neurosci* 24: 6228-6236.

Jensen F E (2002). Relationship between encephalopathy and abnormal neuronal activity in the developing brain. *Int Rev Neurobiol* 49: 23-35.

Keller B U, Blaschke M, Rivosecchi R, Hollmann M, Heinemann S F, Konnerth A (1993). Identification of a subunit-specific antagonist of alpha-amino-3-hydroxy-5-methyl-4-isoxazolepropionate/kainate receptor channels. *Proc Natl Acad Sci USA* 90: 605-609.

Lash L L, Sanders J M, Akiyama N, Shoji M, Postila P, Pentikainen O T, et al. (2008). Novel analogs and stereoisomers of the marine toxin neodysiherbaine with specificity for kainate receptors. *J Pharmacol Exp Ther* 324: 484-496.

Lu W, Shi Y, Jackson A C, Bjorgan K, During M J. Sprengel R, et al. (2009). Subunit composition of synaptic AMPA receptors revealed by a single-cell genetic approach. *Neuron* 62: 254-268.

Maj J, Rogoz Z, Skuza G, Jaros T (1995). Some behavioral effects of CNQX AND NBQX, AMPA receptor antagonists. *Pol J Pharmacol* 47: 269-277.

Malinow R, Malenka R C (2002). AMPA receptor trafficking and synaptic plasticity. *Annu Rev Neurosci* 25: 103-126.

Mayer M L, Westbrook G L (1987). The physiology of excitatory amino acids in the vertebrate central nervous system. *Prog Neurobiol* 28: 197-276.

Mony L, Kew J N, Gunthorpe M J, Paoletti P (2009). Allosteric modulators of NR2B-containing NMDA receptors: molecular mechanisms and therapeutic potential. *Br J Pharmacol* 157: 1301-1317.

Mulle C, Sailer A, Pérez-Otaño I, Dickinson-Anson H, Castillo P E, Bureau I, et al. (1998). Altered synaptic physiology and reduced susceptibility to kainate-induced seizures in GluR6-deficient mice. *Nature* 392: 601-605.

Namba T, Morimoto K, Sato K, Yamada N, Kuroda S (1994). Antiepileptogenic and anticonvulsant effects of NBQX, a selective AMPA receptor antagonist, in the rat kindling model of epilepsy. *Brain Res* 638: 36-44.

Nelson S B, Turrigiano G G (2008). Strength through diversity. *Neuron* 60: 477-482.

Nelson S B, Turrigiano G G (1998). Synaptic depression: a key player in the cortical balancing act. *Nat Neurosci* 1: 539-541.

Nutt J G, Gunzler S A, Kirchhoff T, Hogarth P, Weaver J L, Krams M, et al. (2008). Effects of a NR2B selective NMDA glutamate antagonist, CP-101,606, on dyskinesia and Parkinsonism. *Mov Disord* 23: 1860-1866.

O'Neill M J, Bond A, Ornstein P L, Ward M A, Hicks C A, Hoo K, et al. (1998). Decahydroisoquinolines: novel competitive AMPA/kainate antagonists with neuroprotective effects in global cerebral ischaemia. *Neuropharmacology* 37: 1211-1222.

Oikawa M, Ikoma M, Sasaki M, Gill M B, Swanson G T, Shimamoto K, et al. (2009). Regioselective Domino Metathesis of Unsymmetrical 7-Oxanorborenes with Electron-Rich Vinyl Acetate toward Biologically Active Glutamate Analogues. *European J Org Chem* 2009: 5531-5548.

Pal S, Sombati S, Limbrick D D, Jr., DeLorenzo R J (1999). In vitro status epilepticus causes sustained elevation of intracellular calcium levels in hippocampal neurons. *Brain Res* 851: 20-31.

Parsons C G, Stoffler A, Danysz W (2007). Memantine: a NMDA receptor antagonist that improves memory by restoration of homeostasis in the glutamatergic system—too little activation is bad, too much is even worse. *Neuropharmacology* 53: 699-723.

Patneau D K, Vyklicky L, Jr., Mayer M L (1993). Hippocampal neurons exhibit cyclothiazide-sensitive rapidly desensitizing responses to kainate. *J Neurosci* 13: 3496-3509.

Sanders J M, Ito K, Settimo L, Pentikainen O T, Shoji M, Sasaki M, et al. (2005). Divergent pharmacological activity of novel marine-derived excitatory amino acids on glutamate receptors. *J Pharmacol Exp Ther* 314: 1068-1078.

Smith T, Groom A, Zhu B, Turski L (2000). Autoimmune encephalomyelitis ameliorated by AMPA antagonists. *Nat Med* 6: 62-66.

Stern-Bach Y, Russo S, Neuman M, Rosenmund C (1998). A point mutation in the glutamate binding site blocks desensitization of AMPA receptors. *Neuron* 21: 907-918.

Swanson G T, Sakai R (2009). Ligands for ionotropic glutamate receptors. *Prog Mol Subcell Biol* 46: 123-157.

Szabados T, Gigler G, Gacsalyi I, Gyertyan I, Levay G (2001). Comparison of anticonvulsive and acute neuroprotective activity of three 2,3-benzodiazepine compounds, GYKI 52466, GYKI 53405, and GYKI 53655. *Brain Res Bull* 55: 387-391.

Tan D S (2005). Diversity-oriented synthesis: exploring the intersections between chemistry and biology. *Nat Chem Biol* 1: 74-84.

Vivithanaporn P, Lash L L, Marszalec W, Swanson G T (2007). Critical roles for the M3-S2 transduction linker domain in kainate receptor assembly and postassembly trafficking. *J Neurosci* 27: 10423-10433.

Walters M R, Kaste M, Lees K R, Diener H C, Hommel M, De Keyser J, et al. (2005). The AMPA antagonist ZK 200775 in patients with acute ischaemic stroke: a double-blind, multicentre, placebo-controlled safety and tolerability study. *Cerebrovascular diseases (Basel, Switzerland)* 304-309.

Weigand E, Keller B U (1998). Functional diversity of synaptic AMPA/KA receptors from rat as revealed by subtype-specific antagonists. *Eur J Neurosci* 10: 64-70.

Wilding T J, Huettner J E (1995). Differential antagonism of alpha-amino-3-hydroxy-5-methyl-4-isoxazolepropionic acid-preferring and kainate-preferring receptors by 2,3-benzodiazepines. *Mol Pharmacol* 47: 582-587.

Wong L A, Mayer M L (1993). Differential modulation by cyclothiazide and concanavalin A of desensitization at native alpha-amino-3-hydroxy-5-methyl-4-isoxazolepropionic acid- and kainate-preferring glutamate receptors. *Mol Pharmacol* 44: 504-510.

Wood P L (2005). The NMDA receptor complex: a long and winding road to therapeutics. *IDrugs* 8: 229-235.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A pharmaceutical composition comprising:
(a) a compound having a formula:

or a salt or solvate thereof; and
(b) one or more pharmaceutically acceptable carriers, diluents, or excipients.

2. The composition of claim 1, wherein the composition is suitable for administration to a human.

3. The composition of claim 1, wherein the composition is suitable for oral administration.

4. The composition of claim 1, wherein the composition is suitable for transdermal administration.

* * * * *